United States Patent
Hung et al.

(10) Patent No.: US 6,331,284 B1
(45) Date of Patent: Dec. 18, 2001

(54) P202 IS A TUMOR SUPPRESSOR

(75) Inventors: Mien-Chie Hung; Duen-Hwa Yan; Yong Wen; Bill Spohn, all of Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/590,652

(22) Filed: Jun. 8, 2000

Related U.S. Application Data

(60) Provisional application No. 60/139,039, filed on Jun. 10, 1999.

(51) Int. Cl.[7] .......................... A61K 51/00; A61K 48/00; A61K 38/21; A61K 31/711

(52) U.S. Cl. ..................... 424/1.11; 424/93.1; 424/93.2; 424/93.6; 435/320.1; 435/455; 435/456; 435/458; 514/2; 514/44; 530/350; 536/23.1; 536/23.5; 536/24.1

(58) Field of Search .................. 435/69.1, 320.1, 435/455, 456, 458; 424/93.1, 93.2, 93.6, 278, 1.11; 514/2, 44; 530/350; 536/23.1, 23.5, 24.1

(56) References Cited

PUBLICATIONS

Mountain, TIBTECH, vol. 18, pp. 119–128, Mar. 2000.*
Fox, Nature Biotechnology, vol. 18, pp. 143–144, Feb. 2000.*
Anderson, Nature, vol. 392, pp. 25–30, Apr. 1998.*
Verma et al., Nature, vol. 389, pp. 239–242, Sep. 1997.*
Gura, Science, vol. 278, pp. 1041–1042, Nov. 1997.*
Nielsen et al., Cancer Gene Therapy, vol. 5, No. 1, pp. 52–63, 1998.*
Kmiec, American Scientist, vol. 87, pp. 240–247, May 1999.*
Ahre et al., "High doses of natural α–interferon (α–IFN) in the treatment of multiple myeloma–a pilot study from the myeloma group of central Sweden (MGCS),"*Eur. J. Haematol.*, 41:123–130, 1988.
Beg and Baltimore, "An essential role of NF–κB in preventing TNF–α–induced cell death," *Science*, 274:782–784, 1996.
Boussif et al., "A versatile vector for gene and oligonucleotide transfer into cells in culture and in vivo: polyethylenimine," *Proc. Nat'l. Acad. Sci. USA.*, 92:7297–7301, 1995.
Choubey and Gutterman, "Inhibition of E2F–4/DP–1–stimulated transcription by p202," *Oncogene.*, 15: 291–301, 1997.
Choubey and Gutterman, "The interferon–inducible growth–inhibitory p202 protein: DNA binding properties and identification of a DNA binding domain," *Biochem. Biophys. Res. Commun.*, 221:396–401, 1996.

Choubey and Lengyel, "Binding of an interferon–inducible protein (p202) to the retinoblastoma protein," *J. Biol. Chem.*, 270:6134–6140, 1995.
Choubey et al., "Inhibition of e2f–mediated transcription by p202," *EMBO J.*, 15:5668–5678, 1996.
Choubey et al., "Interferons as gene activators," *J. Biol. Chem.*, 264:17182–17189, 1989.
Choubey, and Lengyel, "Interferon action: cytoplasmic and nuclear localization of the interferon–inducible 52–kD protein that is encoded by the ifi 202 gene from the gene 200 cluster," *J. Interferon. Res.*, 13:43–52, 1993.
Coradini et al., "Activity of tamoxifen and new antiestrogens on estrogen receptor positive and negative,"*Anticancer Res.*, 14:1059–64, 1994.
Coradini et al., "The effect of alpha–, beta– and gamma–interferon on the growth of breast cancer cell lines," *Anticancer Res.*, 14:1779–1784, 1994.
Datta et al., "Increase in p202 expression during skeletal muscle differentiation: inhibition of myod protein expression and activity by p202," *Mol. Cell. Biol.*, 18:1074–1083, 1998.
Datta et al., "P202, an interferon–inducible modulator of transcription, inhibits transcriptional activation by the p53 tumor suppressor protein, and a segment from the p53–binding protein 1 that binds to p202 overcomes this inhibition," *J. Biol. Chem.*, 271:27544–27555, 1996.
Ezekowitz et al., "Interferon alfa–2a therapy for life–threatening hemangiomas of infancy," *N. Engl. J. Med.*, 326:1456–1463, 1992.
Gottardis et al., "Estradiol–stimulated growth of mef–7 tumors implanted in aathymic mice: a model to study the tumoristatic action of tamoxifen," *J. Steroid Biochem.*, 30:311–314, 1988.
Grzegorzewski et al., "Induction of Macrophage tumoricidal activity, major histocompatibility complex class II antigen (Ia[k]) expression, and interleukin–1 production by swainsonine," *Cancer Commun.*, 1:373–379, 1989.
Gutterman and Choubet, "Retardation of cell proliferation after expression of p202 accompanies an increase in p21[waf1/cip11] Cell," *Growth Differ.*, 10:93–100, 1999.
Gutterman, "Cytokine therapeutics: lessons from interferon α," *Proc. Natl. Acad. Sci. U. S. A.*, 91:1198–1205, 1994.
Kirkwood et al., "A randomized study of low and high doses of leukocyte α–interferon in metastatic renal cell carcinoma: the american cancer society collaborative trial," *Cancer Res.*, 45: 863–871, 1985.

(List continued on next page.)

*Primary Examiner*—David Guzo
(74) *Attorney, Agent, or Firm*—Fulbright & Jaworski LLP

(57) ABSTRACT

The present invention relates generally to the fields of cancer therapy and gene therapy. More particularly, the invention demonstrates methods for repressing or preventing transformation and proliferation of tumor cells. The method comprises contacting a cell with a p202 polypeptide in an amount effective to inhibit a transformed phenotype or cell proliferation. Inhibition of transformation may be indicated by a reduction in a transforming, tumorigenic or metastatic potential of a cell.

66 Claims, 15 Drawing Sheets

OTHER PUBLICATIONS

Koul et al., "p202 prevents apoptosis in murine AKR–2B fibroblasts," *Biochem. Biophys. Res. Commun.,* 247:379–382, 1998.

Kull and Cuatrecasas, "Possible requirement of internalization in the mechanism of in vitro cytotoxicity in tumor necrosis serum," *Cancer Res.,* 41:4885–4890, 1981.

Lembo et al., "Constitutive expression of the interferon–inducible protein p202 in nih 3t3 cells affects cell cycle progression," *J. Biol. Regul. Homeost. Agents,* 9 :42–46, 1995.

Min et al., "The interferon–inducible p202 protein as a modulator of transcription: inhibition of NF–κB, c–Fos, and c–Jun activities," *Mol. Cell. Biol.,* 16:359–368, 1996.

Oettgen et al., "Treatment of AIDS–associated kaposi's sarcoma with recombinant alpha interferon," *Immunobiology,* 172: 269–274, 1986.

Sokoloff et al., "In vitro modulation of tumor progression–associated properties of hormone refractory prostate carcinoma cell lines by cytokines," *Cancer,* 77:1862–1872, 1996.

Sugarman et al., "Recombinant human tumor necrosis factor–α: effects on proliferation of normal and tranformed cells in vitro," *Science,* 230:943–945, 1985.

Van Antwerp et al., "Suppression of TNF–α–induced apoptosis by nf–κb," *Science,* 274:787–789, 1996.

Wang et al., "TNF– and cancer therapy–induced apoptosis: potentiation by inhibition of nf–κb," *Science,* 274:784–787, 1996.

Yan et al., "Reduced growth rate and tranformation phenotype of the prostate cancer cells by an interferon–inducible protein, p202," *Oncogene,* 18:807–811, 1999.

\* cited by examiner

SEQUENCE LISTING

<160> NUMBER OF SEQ ID NOS: 2

<210> SEQ ID NO 1
<211> LENGTH: 1857
<212> TYPE: DNA
<213> ORGANISM: Mus musculus

<400> SEQUENCE: 1

| | | | | | |
|---|---|---|---|---|---|
| aagaaatgaa | acaactctga | gagtgttgta | atcactacca | tcttccttta | cacccaactg | 60 |
| ttcagtttct | catttactga | cttatctgcc | tacctactca | agccaagcag | gccacttctt | 120 |
| gacccggtga | aggtctcagg | atctgtacat | cactgcagaa | atatccagga | agctgacaca | 180 |
| ctctgccttg | ttggagatct | aggacccgga | acaggagtca | ctgaagaagt | tcccggcttg | 240 |
| aagaactcaa | tcaaaaagtc | tgtatctaca | gaaagagaca | tctgtcccag | gcaatgtcca | 300 |
| accgtaactt | aaggtcatct | accaactcag | aattttctga | gggtcaacat | cagacccctt | 360 |
| ccagtgattc | atctggccat | ggggaggatc | aacctcaagc | ctctcctgga | cctaacaaaa | 420 |
| agtcacacac | cccaaaaaag | aacattagca | aaggtgctgt | tcttcatgag | aaacccatga | 480 |
| cagtgatggt | actcactgca | acagaaccat | ttaattataa | agagggaaaa | gagaacatgt | 540 |
| tcatgctac | agtggctaca | gagagccaat | attaccgtgt | gaaagttttc | aacatggact | 600 |
| tgaaagagaa | gttcacagaa | aataaattta | ttaccatttc | caaatacttc | aacagcagtg | 660 |
| gcatcctaga | gatcaatgaa | actgccactg | tgtcagaggc | tgctcctaac | caaatgtttg | 720 |
| aagtgcccaa | aaatattatc | agaagtgcaa | aagaaactct | taagatctct | aaaattaaag | 780 |
| aacttgattc | tggaacactg | atttatggtg | tgtttgcagt | agagaagaaa | aaagtgaatg | 840 |
| ataaaagtat | aaccttcaaa | ataaaagata | tgaagataa | tataaaagtg | gtgtgggata | 900 |
| aagaacagca | caatatcaac | tatgagaaag | gagataaact | ccaactcttc | tcctttcacc | 960 |
| tgagaaaagg | aaatgggaaa | ccaatattac | actctggaaa | tcacagtttc | atcaagggag | 1020 |
| aaaagctact | aaaagaatct | tttgaagggg | atggttacca | caaggtccc | aaacaagtgg | 1080 |
| tggcattgaa | agcaacaaaa | ctatttactt | atgatagtat | aaaaagtaaa | aagatgttcc | 1140 |
| atgccacagt | ggctactgat | acagaattct | tcagagtgat | ggtgttcgag | aaaacctag | 1200 |
| agaaaaagtt | tatcccggga | aacaccattg | ctttatcaga | ttattttggt | atgtatgggt | 1260 |
| ctctggcaat | acatgaatat | tccagcgtgt | ctgaggtgaa | gagccaaaat | aaggaagact | 1320 |
| caagttcatc | agatgaaaga | cccatagaac | atcttaaaat | ttgtgatctt | cacttgcaaa | 1380 |
| cagaagaaag | gctgtttgat | ggagagttta | agtatacag | gaaaagttcc | ggaaataatt | 1440 |
| gtatatgcta | tggaatttgg | gatgatacag | gagcaatgaa | agtggtggta | tctggacaac | 1500 |
| tgaccagtgt | caactgtgag | attggtaata | caattagact | tgtctgcttt | gaattgacct | 1560 |
| caaatgcaga | tgagtggttt | ctgagagcta | cgaggtacag | ttacatggag | gtcatcatgc | 1620 |
| ctgaaaaatg | aaaaacagtg | agtgatgtaa | ccccaattca | atggtggaaa | tttccttatg | 1680 |
| aaacatgtac | actgaaaatg | gaaaagaaat | gtatacctgc | tcaaatataa | tacatacaac | 1740 |
| atccagctct | tagttgtggg | aacaatactt | tagcttattc | tttataaaaa | ttttatgaac | 1800 |
| tttcatagtc | tgcatgctta | agtttcataa | tatgaaataa | ataaatgctg | tacatta | 1857 |

<210> SEQ ID NO 2
<211> LENGTH: 445
<212> TYPE: PRT
<213> ORGANISM: Mus musculus

<400> SEQUENCE: 2

```
Met Ser Asn Arg Asn Leu Arg Ser Ser Thr Asn Ser Glu Phe Ser Glu
  1               5                  10                  15
Gly Gln His Gln Thr Pro Ser Ser Asp Ser Ser Gly His Gly Glu Asp
             20                  25                  30
Gln Pro Gln Ala Ser Pro Gly Pro Asn Lys Lys Ser His Thr Pro Lys
         35                  40                  45
Lys Asn Ile Ser Lys Gly Ala Val Leu His Glu Lys Pro Met Thr Val
     50                  55                  60
Met Val Leu Thr Ala Thr Glu Pro Phe Asn Tyr Lys Glu Gly Lys Glu
 65                  70                  75                  80
Asn Met Phe His Ala Thr Val Ala Thr Glu Ser Gln Tyr Tyr Arg Val
                 85                  90                  95
Lys Val Phe Asn Met Asp Leu Lys Glu Lys Phe Thr Glu Asn Lys Phe
            100                 105                 110
Ile Thr Ile Ser Lys Tyr Phe Asn Ser Ser Gly Ile Leu Glu Ile Asn
        115                 120                 125
Glu Thr Ala Thr Val Ser Glu Ala Ala Pro Asn Gln Met Phe Glu Val
    130                 135                 140
Pro Lys Asn Ile Ile Arg Ser Ala Lys Glu Thr Leu Lys Ile Ser Lys
145                 150                 155                 160
Ile Lys Glu Leu Asp Ser Gly Thr Leu Ile Tyr Gly Val Phe Ala Val
                165                 170                 175
Glu Lys Lys Lys Val Asn Asp Lys Ser Ile Thr Phe Lys Ile Lys Asp
            180                 185                 190
Asn Glu Asp Asn Ile Lys Val Val Trp Asp Lys Glu Gln His Asn Ile
        195                 200                 205
Asn Tyr Glu Lys Gly Asp Lys Leu Gln Leu Phe Ser Phe His Leu Arg
    210                 215                 220
Lys Gly Asn Gly Lys Pro Ile Leu His Ser Gly Asn His Ser Phe Ile
225                 230                 235                 240
Lys Gly Glu Lys Leu Leu Lys Glu Ser Phe Glu Gly Asp Gly Tyr His
                245                 250                 255
Lys Gly Pro Lys Gln Val Val Ala Leu Lys Ala Thr Lys Leu Phe Thr
            260                 265                 270
Tyr Asp Ser Ile Lys Ser Lys Lys Met Phe His Ala Thr Val Ala Thr
        275                 280                 285
Asp Thr Glu Phe Phe Arg Val Met Val Phe Glu Glu Asn Leu Glu Lys
    290                 295                 300
Lys Phe Ile Pro Gly Asn Thr Ile Ala Leu Ser Asp Tyr Phe Gly Met
305                 310                 315                 320
Tyr Gly Ser Leu Ala Ile His Glu Tyr Ser Ser Val Ser Glu Val Lys
                325                 330                 335
Ser Gln Asn Lys Glu Asp Ser Ser Ser Asp Glu Arg Pro Ile Glu
            340                 345                 350
His Leu Lys Ile Cys Asp Leu His Leu Gln Thr Glu Glu Arg Leu Phe
        355                 360                 365
Asp Gly Glu Phe Lys Val Tyr Arg Lys Ser Ser Gly Asn Asn Cys Ile
    370                 375                 380
Cys Tyr Gly Ile Trp Asp Asp Thr Gly Ala Met Lys Val Val Ser
385                 390                 395                 400
Gly Gln Leu Thr Ser Val Asn Cys Glu Ile Gly Asn Thr Ile Arg Leu
```

```
                        405                 410                 415
Val Cys Phe Glu Leu Thr Ser Asn Ala Asp Glu Trp Phe Leu Arg Ala
                420                 425                 430
Thr Arg Tyr Ser Tyr Met Glu Val Ile Met Pro Glu Lys
        435                 440                 445
```

P202 IS A TUMOR SUPPRESSOR

The present application claims priority on co-pending U.S. Provisional Patent Application Ser. No. 60/139,039 filed Jun. 10, 1999. The entire text of the above-referenced disclosure is specifically incorporated by reference herein without disclaimer.

The government owns rights in the present invention pursuant to grant numbers RO-1 CA 58880 and CA77858 from the National Institutes of Health.

BACKGROUND OF THE INVENTION

1. Field of the Invention

The present invention relates generally to the fields of cancer therapy and gene therapy. More particularly, it concerns the use of p202 to prevent and treat cell transformation.

2. Description of Related Art

Oncogenesis was described by Foulds (1958) as a multistep biological process, which is presently known to occur by the accumulation of genetic damage. On a molecular level, the multistep process of tumorigenesis involves the disruption of both positive and negative regulatory effectors (Weinberg, 1989). The molecular basis for human colon carcinomas has been postulated, by Vogelstein and coworkers (1990), to involve a number of oncogenes, tumor suppressor genes and repair genes. Similarly, defects leading to the development of retinoblastoma have been linked to another tumor suppressor gene (Lee et al., 1987). Still other oncogenes and tumor suppressors have been identified in a variety of other malignancies. Unfortunately, there remains an inadequate number of treatable cancers, and the effects of cancer are catastrophic—over half a million deaths per year in the United States alone.

Cancer is fundamentally a genetic disease in which damage to cellular DNA leads to disruption of the normal mechanisms that control cellular proliferation. Two of the mechanisms of action by which tumor suppressors maintain genomic integrity is by cell arrest, thereby allowing for repair of damaged DNA, or removal of the damaged DNA by apoptosis (Ellisen and Haber, 1998; Evan and Littlewood, 1998). Apoptosis, otherwise called "programmed cell death," is a carefully regulated network of biochemical events which act as a cellular suicide program aimed at removing irreversibly damaged cells. Apoptosis can be triggered in a number of ways including binding of tumor necrosis factor, DNA damage, withdrawal of growth factors, and antibody cross-linking of Fas receptors (Cohen, 1993; Lowe et al., 1993; Sentman et al., 1991; Smith et al., 1994; Suda et al., 1993; Williams and Smith, 1993). Although several genes have been identified that play a role in the apoptotic process, the pathways leading to apoptosis have not been fully elucidated.

Interferons (IFNs), a family of cytokines, consists of three major glycoproteins, INF-α, INF-β, and INF-γ. IFNs possess a wide variety of biological properties such as antivirus, anti-proliferation, immunoregulation, antiangiogenesis, and anti-neoplasia (Gutterman, 1994). The anti-neoplastic activity of IFNs can be attributed, in part, to their anti-proliferation function and the activation of host defense systems on tumor cells. In addition, the demonstration of anti-angiogenic activity of IFNs has led to clinical trials using IFN treatment for vascular tumors, that include Kaposi sarcoma (Oettgen et al., 1986), pulmonary hemangiomatosis (Grzegorzewski et al., 1989) and hemangioma (Ezekowitz et al., 1992), resulting in tumor regression in these patients. Apart from the therapeutic effects of IFNs in certain clinical settings, there were also undesirable side effects (e.g., fever, chills, anorexia, and anemia) associated with the high dose IFN treatment often required to obtain a significant response (Ahre et al., 1998; Kirkwood et al., 1985).

p202 is a 52 kDa nuclear IFN-inducible phosphoprotein. This protein may inhibit the transcription of certain genes by interacting with various transcription modulators (Choubey et al., 1996; Choubey et al., 1997; Choubey and Lengyel, 1995; Datta et al., Datta et al., 1998; 1996; Min et al., 1996). p202 expression has been associated with an increase in both p21 and Rb and a decrease in Cdk2 protein kinase activity (Gutterman and Coubey, 1999) and constitutive expression of p202 may be associated with cell cycle arrest in mammalian cells (Lembo et al., 1995; Yan et al., 1999).

SUMMARY OF THE INVENTION

The present invention generally relates to methods for repressing or preventing transformation in a cell, the method comprising contacting the cell with a p202 polypeptide in an amount effective to inhibit a transformed phenotype. Inhibition of transformation may be indicated by a reduction in a transforming, tumorigenic, or metastatic potential of a cell. Such cells may be in cell culture. More preferably, the cell in which transformation is to be repressed are cells in a living organism, for example a human. The inhibition of such transformation has great utility in the prevention and treatment of such transformation-driven events as cancer, tumorigenesis, and metastasis.

A p202 polypeptide may be contacted with or introduced to a cell through any of a variety of manners known to those of skill. The p202 polypeptide may be introduced through direct introduction of a p202 polypeptide to a cell. In this case, the p202 polypeptide may be obtained through any method known in the art, although it is expected that in vitro expression of the p202 polypeptide in a cell culture system may be a preferred manner of obtaining p202.

p202 may also be introduced to a cell via the introduction of a polynucleotide that encodes the p202 polypeptide to the cell. For example, RNA or DNA encoding p202 may be introduced to the cell by any manner known in the art. In certain preferred embodiments, the p202 is introduced into the cell through the introduction of a DNA segment which encodes p202. In some such embodiments, it is envisioned that the DNA segment further comprises the p202 gene operatively linked to its associated control sequences. For example, the p202 gene may be operatively linked to a suitable promoter and a suitable terminator sequence. The construction of such gene/control sequence DNA constructs is well-known within the art. In particular embodiments the promoter is selected from the group comprising of CMV IE, SV40 IE, RSV LTR, or β-actin. In certain embodiments for introduction, the DNA segment may be located on a vector, for example, a plasmid vector or a viral vector. The virus vector may be, for example, selected from the group comprising retrovirus, adenovirus, herpesvirus, vaccina virus, and adeno-associated virus. Such a DNA segment may be used in a variety of methods related to the invention. The vector may be used to deliver a p202 gene to a cell in one of the gene-therapy embodiments of the invention. Also, such vectors can be used to transform cultured cells, and such cultured cells could be used, inter alia, for the expression of p202 in vitro.

In particular embodiments the p202 is introduced into a cell that is a human cell. In many embodiments the cell is a tumor cell. In some presently preferred embodiments the tumor cell is a breast tumor cell, a prostrate tumor cell, or an ovarian tumor cell. However, p202 may be introduced into other tumor cells including, but not limited to, a bladder tumor cell, a testicular tumor cell, a colon tumor cell, a skin tumor cell, a lung tumor cell, a pancreatic tumor cell, a stomach tumor cell, an esophageal tumor cell, a brain tumor cell, a leukemia tumor cell, a liver tumor cell, an endometrial tumor cell, or a head and neck tumor cell. In some embodiments, the p202 is introduced by injection.

In some embodiments of the present invention, the inventor's discovery that p202 is able to inhibit transformation will be used in combination with other anti-transformation/ anti-cancer therapies. These other therapies may be known at the time of this application, or may become apparent after the date of this application. p202 may be used in combination with other therapeutic polypeptides, polynucleotides encoding other therapeutic polypeptides, or chemotherapeutic agents. For example, p202 may be used in conjunction with other known polypeptides, such as TNFα or P53. p202 may be used in conjunction with any suitable chemotherapeutic agent. In one representative embodiment, the chemotherapeutic agent is taxol. p202 also may be used in conjunction with radiotherapy. The type of ionizing radiation constituting the radiotherapy may be selected from the group comprising x-rays, γ-rays, and microwaves. In certain embodiments, the ionizing radiation may be delivered by external beam irradiation or by administration of a radionuclide. p202 also may be used with other gene-therapy regimes. In particular embodiments the p202 is introduced into a tumor. The tumor may be in an animal, in particular, a human. The p202 may be introduced by injection.

Another aspect of the present invention is a method for inhibiting tumor cell proliferation, the method comprising contacting a tumor cell with a p202 polypeptide in an amount effective to inhibit tumor cell proliferation. In representative embodiments of the invention, p202 is introduced to the tumor cell through direct introduction of a p202 polypeptide or through the introduction of a polynucleotide encoding a p202 polypeptide.

In some embodiments of the present invention, the inventor's discovery that p202 is able to inhibit tumor cell proliferation will be used in combination with other therapeutic agents. The other therapies may be known at the time of this application, or may become apparent after the date of this application. p202 may be used in combination with other therapeutic polypeptides, polynucleotides encoding other therapeutic polypeptides, chemotherapeutic agents, or radiotherapeutic agents. The p202 may be introduced into a tumor, and the tumor may be contained in an animal, in particular, a human. The p202 may be introduced by injection. In some embodiments, the other therapeutic agent induces apoptosis. In one preferred embodiment, the other agent capable of inducing apoptosis is TNFα. Other polypeptide inducers of apoptosis that may be used in combination with p202 include, but are not limited to, p53, Bax, Bak, Bcl-x, Bad, Bim, Bik, Bid, Harakiri, Ad E1B, Bad and ICE-CED3 proteases. In other embodiments, a chemotherapeutic agent capable of inducing apoptosis is used in combination with p202. In one preferred embodiment, the chemotherapeutic agent capable of inducing apoptosis is taxol. In another embodiment, radiotherapy comprising ionizing radiation is the other apoptosis-inducing therapeutic agent. The type of ionizing radiation may be selected from the group comprising x-rays, γ-rays, and microwaves. The ionizing radiation may be delivered by external beam irradiation or by administration of a radionuclide.

Another aspect of the present invention, is a method for altering the phenotype of a tumor cell comprising contacting a tumor cell with a p202 polypeptide in an amount effective to alter the phenotype of the tumor cell. The phenotype of the tumor cell may be selected from a group comprising, but not limited to, proliferation, soft agar growth, migration, contact inhibition or cell cycling. In some embodiments, the tumor cell is may be in a tumor. In particular embodiments, the tumor is in an animal, in particular, a human. The p202 polypeptide may be introduced by injection.

The p202 gene products and polynucleotides of the present invention may also be introduced using any suitable method. A "suitable method" of introduction is one that places a p202 gene product in a position to inhibit the transformation of a cell, reduce the proliferation of a tumor cell, or alter the phenotype of a tumor cell. For example, injection, oral, and inhalation methods may be employed, with the skill artisan being able to determine an appropriate method of introduction for a given circumstance. In some preferred embodiments, injection will be used. This injection may be intravenous, intraperitoneal, intramuscular, subcutaneous, intratumoral, intrapleural, or of any other appropriate form.

In certain other aspects of the present invention there are provided therapeutic kits comprising in suitable container, a pharmaceutical formulation of a p202 gene product or a polynucleotide encoding a p202 gene product. Such a kit may further comprise a pharmaceutical formulation of a therapeutic polypeptide, polynucleotide encoding a therapeutic polypeptide, or chemotherapeutic agent.

In keeping with long-standing patent law convention, the words "a," and "an" when used in the present specification in concert with the word comprising, including the claims, denote "one or more."

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A and FIG. 2B: Growth rate of the cell lines was assessed by CyQuant assay. The quantity of both RNA and DNA was measured by using reagents and protocol contained in the CyQuant Cell Proliferation Assay kit. Each measurement was conducted in quadruplicates. FIG.

2C and FIG. 2D: Growth rate of the cell lines determined by the MTT assay. FIGS. 2E and 2F, DNA synthesis rate. The p202 transfectants and the control cells were spread or 96-well plates at $1 \times 10^4$ cells/well. DNA synthesis rate was measured by determining the amount of [$^3$H]-thymidine incorporated into the cells at the time as indicated. The measurement was conducted in quadruplicates.

FIG. 5A: Apoptosis induced by TNF-α. MDA-MB-453 and 453-p202 cells were treated with 20 ng/ml of TNF-α for 48 h. Then treated and untreated cells were fixed and stained with propidium iodide. Apoptosis was quantified by FACScan cytometer. FIG. 5B: Viability assay after serum withdrawal. MDA-MB-453 and 453-p202 cells were transfected with 1 μg of DNA made up of 0.5 μg of pCMV-luciferase reporter plus 0.5μg of pCMV-β-galactosidase. 24 h after transfection, cells were maintained in either serum free medium or complete medium for 48 h. β-galactosidase normalized luciferase activity was measured as an index of cell viability. The values of viability by serum starvation are expressed as the percentage relative to that in complete medium. FIG. 5C: Apoptosis induced by serum depletion. MDA-MB-453 and 453-p202 cells were maintained in serum free medium for 48 h, then fixed and stained with propidium iodide. The stained cells were analyzed on a FACScan cytometer. For transient transfection, MDA-MB-453 cells were transfected with either pcDNA3 vector or p202 expression vector using lipofectin. After 24 h of transfection, the cells were split into two aliquots. One is staved for 48 h, and one is maintained in complete culture medium. Apoptosis was measured as above.

FIG. 6A, p202 expression represses NF-κB-mediated transcription activation in response to TNF-α. MDA-MB-453 cells were co-transfected with IκB-Luciferase reporter gene (κB-luc) (0.2 μg) and CMV-p202 (0, 0.8, or 2 μg) in the presence and absence of TNF-α (20 ng/ml). The fold difference in κB-luc expression was calculated with respect to κ-luc expression in the absence of TNF-α and p202. FIG. 6B, p202 expression represses Rel-A (p65)-activated transcription. MDA-MB-453 cells were co-transfected with κ-luc and±NF-κB (p65) expression vector. The inhibitory activity of p202 on the induction of IκB promoter activity by p65 was assessed by co-transfection with p202 expression vector. The transfected cells were maintained in culture for 48 h and then harvested to measure luciferase activity, and which are presented as average of two independent experiments (±SE) after normalization. FIG. 6C, electrophoretic mobility shift assay. 453 and 453-p202 cells were treated with 20 ng/ml of TNF-α for 30 min., or serum starvation for 24 h, followed by nuclear extract isolation. The activated NF-κB (p65/p50) induced by TNF-α is indicated by an arrow. Competition assay was performed in the presence of a wild type or mutant oligonucleotide. A polyclonal Rel-A antibody super-shifted the NF-κB complex to a slower-migrating position as indicated. FIG. 6D, p202 physically associated with p65. 453 and 453-p202 cells were treated with or without TNF-α (20 ng/ml) for 30 min. Cell lysates (1 mg) were obtained for the subsequent immunoprecipitation with antibody against p65. hmnunoprecipitated complexes were separated by SDS-PAGE followed by immunoblotting with p202 antibody. Immunoblots of 453 and 453-p202 serves as negative and positive control for p202 expression, respectively. The p202 bands are indicated.

FIG. 9A: The growth rate was measured by cell number versus time of growth. FIG. 9B: The DNA synthesis rate was measured by [$^3$H] thymidine incorporation versus time of growth.

FIG. 11A: Reduced tumorigenicity of p202-expressing PC-3 cells. Nude mice were injected subcutaneously with $1 \times 10^5$ cells in each of the two sides of the abdomen. Tumor size was measured each wk and the tumor volume was calculated using the formula: $0.5 \times S^2 \times L$, where S=the short length of the tumor, L=the long length of the tumor. FIG. 11B: p202 reduces the tumorigenicity of PC-3 cells ex vivo. PC-cells were transfected with CMV-p202 using either PEI or LPD liposome, or without liposome (DNA control). Eighteen h after transfection, $1 \times 10^6$ cells were subcutaneously injected in both sides of the abdomen of a nude mouse.

FIG. 12A: Western blot screening the p202 stable transfectants. The G418 resistant colonies from p202 transfection were randomly picked up and analyzed for p202 expression. The 52 kDa protein represents p202 and the non-specific 68 kDa protein cross-reacting with the antibody was used as an equal loading control. Two p202 expressing clones were identified. The p202 expression of p202-2 is extremely low.

FIG. 13A: Soft agar assay. The colonies formed in soft agar of p202 expressing cells and the control cells were stained by p-iodonitrotetrazolium and scored under a microscope.

FIG. 14A: Tumorigenicity assay. p202 stable transfectants or control cells were inoculated subcutaneously with $1 \times 10^6$ cells on each side of nude mice abdomens. Tumor size was measured weekly and tumor volume was calculated. p202 reduces the tumorigenicity of panc-1 cells.

DETAILED DESCRIPTION

Figure 1:
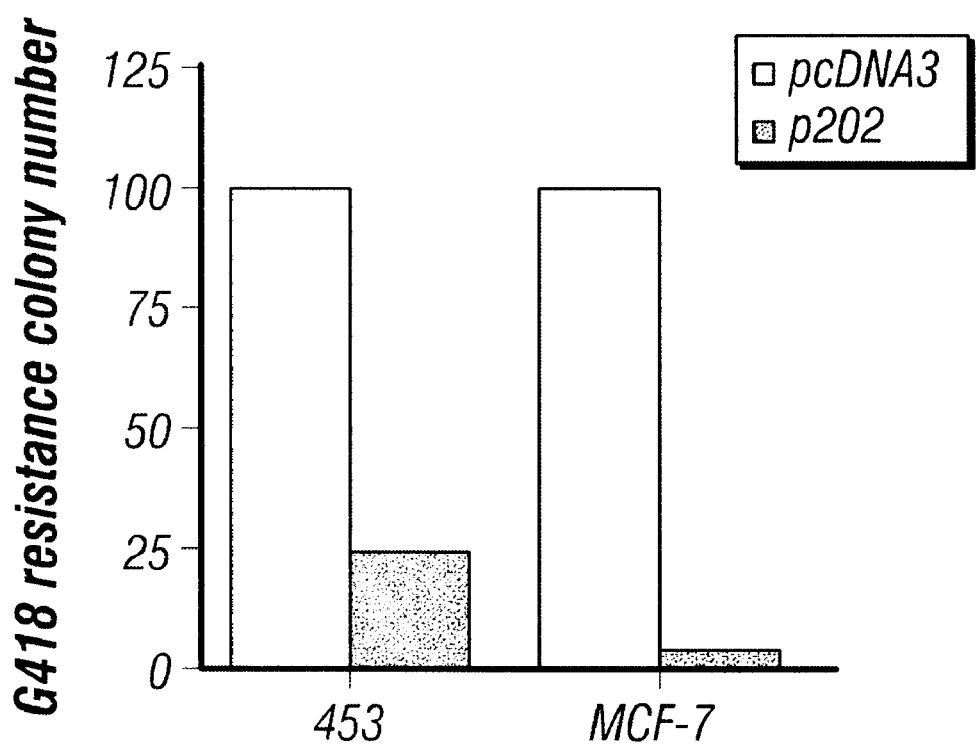
FIG. 1, Expression of p202 inhibits the proliferation of MDA-MB-453 and MCF-7 breast cancer cells. Colony forming assay. MDA-MB-453 and MCF-7 cells were transfected with either a control vector (pcDNA3) or a p202 expression vector. After three weeks of selection, the G418-resistant colonies were visualized by crystal violet and the quantitation is shown whereby the colony number obtained from pcDNA3 transfections were set as 100%.

The present invention describes that expression of p202 inhibits the transformation phenotype, proliferation and tumorigenicity of tumor cells. p202-mediated growth retardation primarily resulted from a reduced rate of cell replication and was not associated with a significant rate of apoptosis. But p202 expression did result in the sensitization of tumor cells to apoptotic agents such as TNFα, taxol and ionizing radiation.

The present invention contemplates the use of p202 to inhibit and/or alter the transformation phenotype of a tumor cell and inhibit tumor cell proliferation. The present invention further contemplates that p202 may be used in combination with one or more anti-cancer/anti-tumor therapeutic agents.

A. Definitions and Techniques Affecting Gene Products and Genes

1. P202 Gene Products and Genes

In this patent the terms "p202 gene product" and "p202" refer to proteins and polypeptides having amino acid sequences which are substantially identical to the native p202 amino acid sequences or which are biologically active in that they are capable of binding to p202 ligands or cross-reacting with anti-p202 antibody raised against p202. Such sequences are disclosed, for example, in Choubey et al., (1989). SEQ ID NO:1 discloses the nucleotide sequence for mouse p202 gene. SEQ ID NO:2 discloses the amino acid sequence for mouse p202 gene product. The term "p202 gene product" also includes analogs of p202 molecules which exhibit at least some biological activity in common with native p202. Such analogs include, but are not limited to, truncated p202 polypeptides and p202 polypeptides having fewer amino acids than native p202. Furthermore, those skilled in the art of mutagenesis will appreciate that homologs to the mouse p202 gene, including human homologs, which homologes are as yet undisclosed or undiscovered, may be used in the methods and compositions disclosed herein.

The invention contemplates a mini-p202 gene product comprising at least the N-terminal domain of a p202 gene product. Such a mini-p202 gene product may further comprise a spacer domain and/or a C-terminal domain of the p202-gene product.

The term "p202 gene" refers to any DNA sequence that is substantially identical to a DNA sequence encoding an p202 gene product as defined above. The term also refers to RNA, or antisense sequences compatible with such DNA sequences. A "p202 gene" may also comprise any combination of associated control sequences.

The term "substantially identical", when used to define either a p202 amino acid sequence or p202 gene polynucleotide sequence, means that a particular subject sequence, for example, a mutant sequence, varies from the sequence of natural p202 by one or more substitutions, deletions, or additions, the net effect of which is to retain at least some biological activity of the p202 protein. Alternatively, DNA analog sequences are "substantially identical" to specific DNA sequences disclosed herein if: (a) the DNA analog sequence is derived from coding regions of the natural p202 gene; or (b) the DNA analog sequence is capable of hybridization of DNA sequences of (a) under moderately stringent conditions and which encode biologically active p202; or (c) DNA sequences which are degenerative as a result of the genetic code to the DNA analog sequences defined in (a) or (b). Substantially identical analog proteins will be greater than about 80% similar to the corresponding sequence of the native protein. Sequences having lesser degrees of similarity but comparable biological activity are considered to be equivalents. In determining polynucleotide sequences, all subject polynucleotide sequences capable of encoding substantially similar amino acid sequences are considered to be substantially similar to a reference polynucleotide sequence, regardless of differences in codon sequence.

2. Percent Similarity

Percent similarity may be determined, for example, by comparing sequence information using the GAP computer program, available from the University of Wisconsin Geneticist Computer Group. The GAP program utilizes the alignment method of Needleman et al., 1970, as revised by Smith et al., 1981. Briefly, the GAP program defines similarity as the number of aligned symbols (i.e. nucleotides or amino acids) which are similar, divided by the total number of symbols in the shorter of the two sequences. The preferred default parameters for the GAP program include (1) a unitary comparison matrix (containing a value of 1 for identities and 0 for non-identities) of nucleotides and the weighted comparison matrix of Gribskov et al., 1986, (2) a penalty of 3.0 for each gap and an additional 0.01 penalty for each symbol and each gap; and (3) no penalty for end gaps.

3. Polynucleotide Sequences

In certain embodiments, the invention concerns the use of p202 genes and gene products, such as the p202 that includes a sequence which is essentially that of the known p202 gene, or the corresponding protein. The term "a sequence essentially as p202" means that the sequence substantially corresponds to a portion of the p202 gene and has relatively few bases or amino acids (whether DNA or protein) which are not identical to those of p202 (or a biologically functional equivalent thereof, when referring to proteins). The term "biologically flictional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of p202 will be sequences which are "essentially the same".

p202 genes which have functionally equivalent codons are also covered by the invention. The term "functionally equivalent codon" is used herein to refer to codons that encode the same amino acid, such as the six codons for arginine or serine, and also refers to codons that encode biologically equivalent amino acids (Table 1).

TABLE 1

FUNCTIONALLY EQUIVALENT CODONS.

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic Acid | Asp | D | GAC | GAU | | | | |
| Glutamic Acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCU | | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It will also be understood that amino acid and polynucleotide sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to polynucleotide sequences which may, for example, include various non-coding sequences flanking either of the 5' or 3' portions of the coding region or may include various internal sequences, i.e., introns, which are known to occur within genes.

In certain embodiments, the invention concerns the use of truncated p202 genes or polynucleotide sequences that encode a p202 polypeptide with less amino acids than native p202. The present invention also encompasses the use of DNA segments which are complementary, or essentially complementary, to the sequences set forth in the specification. Polynucleotide sequences which are "complementary" are those which are capable of base-pairing according to the standard Watson-Crick complementarily rules. As used herein, the term "complementary sequences" means polynucleotide sequences which are substantially complementary, as may be assessed by the same nucleotide comparison set forth above, or as defined as being capable of hybridizing to the polynucleotide segment in question under relatively stringent conditions such as those described herein.

4. Biologically Functional Equivalents

As mentioned above, modification and changes may be made in the structure of p202 and still obtain a molecule having like or otherwise desirable characteristics. For example, certain amino acids may be substituted for other amino acids in a protein structure without appreciable loss of interactive binding capacity with p202 ligands. Since it is the interactive capacity and nature of a protein that defines that protein's biological functional activity, certain amino acid sequence substitutions and/or deletions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of the p202 proteins or peptides (or underlying DNA) without appreciable loss of their biological utility or activity. Included in such changes are truncated p202 polypeptides and p202 polypeptides having less amino acid residues than native p202.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where any changes in p202 that render the polypeptide incapable of suppressing transformation and inhibiting tumor cell proliferation would result in a loss of utility of the resulting peptide for the present invention.

Amino acid substitutions, such as those which might be employed in modifying p202 are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alaanine, glycine and serine; and phenylalanine, tryptophan and tyrosine; are defined herein as biologically fimctional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteinelcystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

5. Sequence Modification Techniques

Modifications to the p202 peptides may be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes the p202 gene. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected gene using site-directed mutagenesis is provided as a means of producing potentially useful p202 and is not meant to be limiting as there are other ways in which sequence variants of these peptides may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

6. Antisense Constructs

In some cases, mutant tumor suppressors may not be non-functional. Rather, they may have aberrant functions that cannot be overcome by replacement gene therapy, even where the "wild-type" molecule is expressed in amounts in excess of the mutant polypeptide. Antisense treatments are one way of addressing this situation. Antisense technology also may be used to "knock-out" function of p202 in the development of cell lines or transgenic mice for research, diagnostic and screening purposes.

Antisense methodology takes advantage of the fact that nucleic acids tend to pair with "complementary" sequences. By complementary, it is meant that polynucleotides are those which are capable of base-pairing according to the standard Watson-Crick complementarily rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarily to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

7. Synthetic Polypeptides

The present invention also describes p202 proteins and related peptides for use in various embodiments of the present invention. The p202 polypeptide may have fewer amino acids than native p202. Relatively small peptides can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

8. Other Structural Equivalents

In addition to the p202 peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

B. Expression Vectors

In certain aspects of the present invention it may be necessary to express the p202 proteins. Throughout this application, the term "expression construct" is meant to include any type of genetic construct containing a polynucleotide coding for a gene product in which part or all of the polynucleotide encoding sequence is capable of being transcribed. The transcript may be translated into a protein, but it need not be. Thus, in certain embodiments, expression includes both transcription of a p202 gene and translation of a p202 mRNA into a p202 protein product. In other embodiments, expression only includes transcription of the polynucleotide encoding a p202 or its complement.

In order for the construct to effect expression of at least a p202 transcript, the polynucleotide encoding the p202 polynucleotide will be under the transcriptional control of a promoter. A "promoter" refers to a DNA sequence recognized by the synthetic machinery of the host cell, or introduced synthetic machinery, that is required to initiate the specific transcription of a gene. The phrase "under transcriptional control" means that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a p202 polynucleotide is not believed to be critical, so long as it is capable of expressing the polynucleotide in the targeted cell at sufficient levels. Thus, where a human cell is targeted, it is preferable to position the polynucleotide coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of the p202 polynucleotide. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosinase (melanoma), alpha-fetoprotein and albumin (liver tumors), CC10 (lung tumor) and prostate-specific antigen (prostate tumor) will permit tissue-specific expression of p202 polynucleotides. Table 2 lists several elements/promoters which may be employed, in the context of the present invention, to regulate the expression of p202 constructs. This list is not intended to be exhaustive of all the possible elements involved in the promotion of p202 expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a p202 construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

TABLE 2

| ENHANCER |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |

TABLE 2-continued

| ENHANCER |
|---|
| τ-Globin |
| β-Globin |
| c-fos |
| c-HA-ras |
| Insulin |
| Neural Cell Adhesion Molecule (NCAM) |
| α$_1$-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

Further, selection of a promoter that is regulated in response to specific physiologic signals can permit inducible expression of the p202 construct. For example, with the polynucleotide under the control of the human PAI-1 promoter, expression is inducible by tumor necrosis factor. Table 3 illustrates several promoter/inducer combinations:

TABLE 3

| Element | Inducer |
|---|---|
| MT 11 | Phorbol Ester (TFA) Heavy metals |
| MMTV (mouse mammary tumor virus) | Glucocorticoids |
| β-Interferon | Poly(rI)X |
| | Poly(rc) |
| Adenovirus 5 E2 | Ela |
| c-jun | Phorbol Ester (TPA), H$_2$O$_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |

In certain embodiments of the invention, the delivery of an expression vector in a cell may be identified in vitro or in vivo by including a marker in the expression vector. The marker would result in an identifiable change to the transfected cell permitting easy identification of expression. Usually the inclusion of a drug selection marker aids in cloning and in the selection of transformants. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed along with the polynucleotide encoding p202. Further examples of selectable markers are well known to one of skill in the art.

One typically will include a polyadenylation signal to effect proper polyadenylation of the transcript. The nature of the polyadenylation signal is not believed to be crucial to the successful practice of the invention, and any such sequence may be employed. The inventor has employed the SV40 polyadenylation signal in that it was convenient and known to function well in the target cells employed. Also contemplated as an element of the expression construct is a terminator. These elements can serve to enhance message levels and to minimize read through from the construct into other sequences.

The expression construct may comprise a virus or engineered construct derived from a viral genome. The ability of certain viruses to enter cells via receptor-mediated endocytosis and, in some cases, integrate into the host cell chromosomes, have made them attractive candidates for gene transfer in to mammalian cells. However, because it has been demonstrated that direct uptake of naked DNA, as well as receptor-mediated uptake of DNA complexes, expression vectors need not be viral but, instead, may be any plasmid, cosmid or phage construct that is capable of supporting expression of encoded genes in mammalian cells, such as pUC or Bluescript™ plasmid series.

C. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for p202 or a fragment thereof. This could be accomplished by x-ray crystallograph, computer modeling or by a combination of both approaches. An alternative approach, "alanine scan," involves the random replacement of residues throughout molecule with alanine, and the resulting affect on function determined.

It also is possible to isolate a p202 specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved p202 activity or which act as stimulators, inhibitors, agonists, antagonists or p202 or molecules affected by p202 function. By use of cloned p202 sequences, sufficient amounts of p202 can be produced to perform crystallographic studies. In addition, knowledge of the polypeptide sequences permits computer employed predictions of structure-function relationships.

The present invention also contemplates the use of p202 and active fragments, and nucleic acids coding therefor, in the screening of compounds for activity in either stimulating p202 activity, overcoming the lack of p202 or blocking the effect of a mutant p202 molecule.

The present invention also encompasses the use of various animal models. By developing or isolating mutant cells lines that fail to express normal p202, one can generate cancer models in mice that will be highly predictive of cancers in humans and other mammals. These models may employ the orthotopic or systemic administration of tumor cells to mimic primary and/or metastatic cancers. Alternatively, one may induce cancers in animals by providing agents known to be responsible for certain events associated with malignant transformation and/or tumor progression. Finally, transgenic animals (discussed below) that lack a wild-type p202 may be utilized as models for cancer development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

D. In Vivo Delivery and Treatment Protocols

Where the gene itself is employed to introduce the gene products, a convenient method of introduction will be through the use of a recombinant vector which incorporates the desired gene, together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding the p202 gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the p202 will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

For introduction of the p202 gene, it is proposed that one will desire to preferably employ a vector construct that will deliver the desired gene to the affected cells. This will, of course, generally require that the construct be delivered to the targeted tumor cells, for example, breast, genital, or lung tumor cells. It is proposed that this may be achieved most preferably by introduction of the desired gene through the use of a viral or non viral vectors to carry the p202 sequences to efficiently transfect the tumor, or pretumorous tissue. This infection may be achieved preferably by liposomal delivery but may also be via adenoviral, a retroviral, a vaccinia virus, herpesvirus or adeno-associated virus vector. These vectors have been successfully used to deliver desired sequences to cells and tend to have a high infection efficiency.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

1. Liposomal Transfection

Thus the expression construct may be entrapped in a liposome. Liposomes are structures created by mixing phospholipids with water, or hydration of phospholipid. The resultant bilayer structures tend to fold back upon themselves. Liposomes are frequently multilamellar, composed of concentric bilayer membranes separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

The present invention also provides particularly useful methods for introducing p202 gene products into cells. One method of in vivo gene transfer which can lead to expression of genes transfected into cells involves the use of liposomes. Liposomes can be used for both in vitro and in vivo transfection. Liposome-mediated gene transfer seems to have great potential for certain in vivo applications in animals (Nicolau et al., 1987). Studies have shown that intravenously injected liposomes are taken up essentially in the liver and the spleen, by the macrophages of the reticuloendothelial system. The specific cellular sites of uptake of injected liposomes appears to be mainly spleen macrophages and liver Kupffer cells. Intravenous injection of liposomes/DNA complexes can lead to the uptake of DNA by these cellular sites, and result in the expression of a gene product encoded in the DNA (Nicolau, 1982).

The inventors contemplate that p202 gene products can be introduced into cells using liposome-mediated gene transfer. It is proposed that such constructs can be coupled with liposomes and directly introduced via a catheter, as described by Nabel et al. (1990). By employing these methods, p202 gene products can be expressed efficiently at a specific site in vivo, not just the liver and spleen cells which are accessible via intravenous injection. Therefore, this invention also encompasses compositions of DNA constructs encoding a p202 gene product formulated as a DNA/liposome complex and methods of using such constructs.

Liposomal transfection can be via liposomes composed of, for example, phosphatidylcholine (PC), phosphatidylserine (PS), cholesterol (Chol), N-[1-(2,3-dioleyloxy) propyl]-N,N-trimethylammonium chloride (DOTMA), dioleoylphosphatidyl-ethanolamine (DOPE), and/or 3β[N-(N'N'-dimethylaminoethane)-carbarmoyl cholesterol (DC-Chol), as well as other lipids known to those of skill in the art. Those of skill in the art will recognize that there are a variety of liposomal transfection techniques which will be useful in the present invention. Among these techniques are those described in Nicolau et al., 1987, Nabel et al., 1990, and Gao et al., 1991. In one embodiment of the present invention, liposomes comprising DC-Chol and DOPE which have been prepared following the teaching of Gao et al., 1991, are used. The inventors also anticipate utility for liposomes comprised of DOTMA, such as those which are available commercially under the trademark Lipofectin™, from Vical, Inc., in San Diego, Calif.

Liposomes may be introduced into contact with cells to be transfected by a variety of methods. In cell culture, the liposome-DNA complex can simply be dispersed in the cell culture solution. For application in vivo, liposome-DNA complex are typically injected. Intravenous injection allow liposome-mediated transfer of DNA complex, for example, the liver and the spleen. In order to allow transfection of DNA into cells which are not accessible through intravenous injection, it is possible to directly inject the liposome-DNA complexes into a specific location in an animal's body. For example, Nabel et al. teach injection via a catheter into the arterial wall. In another example, the inventors have used intraperitoneal injection to allow for gene transfer into mice.

The present invention also contemplates compositions comprising a liposomal complex. This liposomal complex will comprise a lipid component and a DNA segment encoding a p202 gene.

The lipid employed to make the liposomal complex can be any of the above-discussed lipids. In particular, DOTMA, DOPE, and/or DC-Chol may form all or part of the liposomal complex. The inventors have had particular success with complexes comprising DC-Chol. In a preferred embodiment, the lipid will comprise DC-Chol and DOPE. While any ratio of DC-Chol to DOPE is expected to have utility, it is expected that those comprising a ratio of DC-Chol:DOPE between 1:20 and 20:1 will be particularly advantageous. The inventors have found that liposomes prepared from a ratio of DC-Chol:DOPE of about 1:10 to about 1:5 have been useful.

It is proposed that it will ultimately be preferable to employ the smallest region needed to suppress the p202 gene so that one is not introducing unnecessary DNA into cells which receive a p202 gene construct. Techniques well known to those of skill in the art, such as the use of restriction enzymes, will allow for the generation of small regions of p202. The ability of these regions to inhibit tumor cell proliferation, tumorigenicity and transformation phenotype can easily be determined by the assays reported in the Examples.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of polynucleotide in vitro and in vivo, then they are applicable for the present invention. Where a bacterial promoter is employed in the DNA construct, it also will be desirable to include within the liposome an appropriate bacterial polymerase.

2. Adenovirus

Another method for in vivo delivery involves the use of an adenovirus vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

Adenovirus is a particularly suitable gene transfer vector because of its midsized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, located at 16.8 m$\mu$ is particularly efficient during the late phase of infection, and all the mnRNA's issued from this promoter possess a 5'-tripartite leader (TL) sequence which makes them preferred mRNA's for translation.

In some cases, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

A particular method of introducing the p202 to an animal is to introduce a replication-deficient adenovirus containing the p202 gene. The replication-deficient construct made by E1B and E3 deletion also avoids the viral reproduction inside the cell and transfer to other cells and infection of other people, which means the viral infection activity is shut down after it infects the target cell. The p202 gene is still expressed inside the cells. Also, unlike retrovirus, which can only infect proliferating cells, adenovirus is able to transfer the p202 gene into both proliferating and non-proliferating cells. Further, the extrachromosomal location of adenovirus in the infected cells decreases the chance of cellular oncogene activation within the treated animal.

Introduction of the adenovirus containing the p202 gene product gene into a suitable host is typically done by injecting the virus contained in a buffer.

The nature of the adenovirus vector is not believed to be crucial to the successful practice of the invention. Of course, as discussed above, it is advantageous if the adenovirus vector is replication defective, or at least conditionally defective, The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Adenovirus is easy to grow and manipulate and exhibits broad host range in vitro and in vivo. This group of viruses can be obtained in high titers, e.g., $10^9$–$10^{11}$ plaque-fonning units per ml, and they are highly infective. The life cycle of adenovirus does not require integration in to the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus have been used in eukaryotic gene expression (Levrero et al., 1991; Gomez-Foix et al., 1992) and vaccine development (Grunhaus and Horwitz, 1992; Graham and Prevec, 1992). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotatic inoculation into the brain (Le Gal La Salle et al., 1993).

3. Retroviruses

The retroviruses are a group of single-stranded RNA viruses characterized by an ability to convert their RNA to double-stranded DNA to infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed $\psi$ components is constructed (Mann et al., 1983). When a recombinant plasmid containing a human cDNA, together with the retroviral LTR and $\psi$ sequences is introduced into this cell line (by calcium phosphate precipitation for example), the $\psi$ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. One limitation to the use of retrovirus vectors in vivo is the limited ability to produce retroviral vector titers greater than $10^6$ infections U/mL. Titers 10- to 1,000-fold higher are necessary for many in vivo applications.

Several properties of the retrovirus have limited its use in lung cancer treatment (Stratford-Perricaudet and Perricaudet, 1991; (i) Infection by retrovirus depends on host cell division. In human cancer, very few mitotic cells can be found in tumor lesions. (ii) The integration of retrovirus into the host genome may cause adverse effects on target cells, because malignant cells are high in genetic instability. (iii) Retrovirus infection is often limited by a certain host range. (iv) Retrovirus has been associated with many malignancies in both mammals and vertebrates. (v) The titer of retrovirus, in general, is 100- to 1,000-fold lower than that of adenovirus.

4. Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. They offer several attractive features for various mammalian cells (Friedmann, 1989; Ridgeway, 1988; Baichwal and Sugden, 1986; Coupar et al., 1988; Howrich et al., 1990).

With the recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Cultures media containing high titers of the recombinant virus were used to infect primary duckling hepatocytes. Stable CAT gene expression was detected for at least 24 days after transfection (Chang et al., 1991).

5. Other Non-viral Vectors

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. As described above, delivery may be via viral infection where the expression construct is encapsidated in an infectious viral particle.

Several non-viral methods for the transfer of expression constructs into cultured mammalian cells also are contemplated by the present invention. These include calcium phosphate precipitation (Grahan and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the polynucleotide encoding the gene of interest may be positioned and expressed at different sites. In certain embodiments, the polynucleotide encoding the gene may be stably maintained in the cell as a separate, episomal segment of DNA. Such polynucleotide segments or "episomes" encode sequences sufficient to permit maintenance and replication independent of or in synchronization with the host cell cycle. How the expression construct is delivered to a cell and where in the cell the polynucleotide remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer permeabilize the cell membrane. This is particularly applicable for transfer in vitro but it may be applied to in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Reshef (1986) also demonstrated that direct intraperitoneal injection of $CaPO_4$ precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

Other expression constructs which can be employed to deliver a polynucleotide encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific.

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). A synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a polynucleotide encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a polynucleotide encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a polynucleotide into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

6. Protein Therapy

Another therapy approach is the provision, to a subject, of p202 polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

E. Combined Therapy Protocols

Tumor cell resistance to anti-cancer agents represents a major problem in clinical oncology. The present invention may also be used in combination with conventional therapies to improve the efficacy of chemo- and radiotherapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that p202 therapy could be used similarly in conjunction with chemo- or radiotherapeutic intervention.

To kill cells, such as malignant or metastatic cells, using the methods and compositions of the present invention, one would generally contact a "target" cell with a p202 composition and at least one anti-cancer agent. These compositions would be provided in a combined amount effective to kill or inhibit proliferation of the cell. This process may involve contacting the cells with the p202 composition and the anti-cancer agent(s) or factor(s) at the same time. This may be achieved by contacting the cell with a single composition or pharmacological formulation that includes both agents, or by contacting the cell with two distinct compositions or formulations, at the same time, wherein one composition includes the p202 composition and the other includes the anti-cancer agent.

Alternatively, the p202 treatment may precede or follow the anti-cancer agent treatment by intervals ranging from min to weeks. In embodiments where the anti-cancer agent and p202 are applied separately to the cell, one would generally ensure that a significant period of time did not expire between the time of each delivery, such that the anti-cancer agent and p202 composition would still be able to exert an advantageously combined effect on the cell. In such instances, it is contemplated that one would contact the cell with both agents within about 6 h to one wk of each other and, more preferably, within about 24–72 h of each other, with a delay time of only about 48 h being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the p202 or the anti-cancer agent will be desired. Various combinations may be employed, where p202 is "A" and the anti-cancer agent is "B":

| A/B/A | B/A/B | B/B/A | A/A/B | B/B/B/A | B/B/A/B |
|---|---|---|---|---|---|
| A/A/B/B | A/B/A/B | A/B/B/A | B/B/A/A | B/A/B/A | B/A/A/B |
| A/A/A/B | B/A/A/A | A/B/A/A | A/A/B/A | A/B/B/B | B/A/B/B |

To achieve cell killing, both agents are delivered to a cell in a combined amount effective to kill the cell.

In one representative embodiment of the present invention, the anti-cancer agent is taxol (paclitaxel). This agent has proved has proved to be effective for the treatment of patients with metastatic breast or ovarian cancer, and has potential for patients with cervical or endometrial cancer. The regimen of paclitaxel administration has varied in clinical trials, the most common including a dosage of between 135 and 250 mg/m$^2$ administered over an infusion period of 3 or 24 h once every 3 weeks (Wiseman and Spencer, 1998). Promising results have been achieved in phase I/II trials of a weekly regimen of paclitaxel (60 to 175 mg/m2). The objective response rate in patients with metastatic breast cancer (either pretreated or chemotherapy-naive) is generally between 20 and 35% with paclitaxel monotherapy, which compares well with that of other current treatment options including the anthracycline doxorubicin. Combination therapy with paclitaxel plus doxorubicin appears superior to treatment with either agent alone in terms of objective response rate and median duration of response (Wiseman and Spencer, 1998). The present invention contemplates the use of p202 combined with taxol and the use of p202 combined with taxol plus other anti-cancer agents such as doxorubicin.

Many anti-cancer agents are DNA damaging agents. DNA damaging agents or factors are defined herein as any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety chemotherapeutic agents function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. Many DNA damaging agents induce apoptosis. One aspect of the present invention is the use of p202 to sensitize tumor cells to apoptotic agents.

In treating cancer according to the invention, one would contact the tumor cells with a DNA damaging agent in addition to the p202 composition. This may be achieved by irradiating the localized tumor site with DNA damaging radiation such as X-rays, UV-light, γ-rays or even microwaves. Alternatively, the tumor cells may be contacted with the DNA damaging agent by administering to the subject a therapeutically effective amount of a pharmaceutical composition comprising a DNA damaging compound such as, adriamycin, 5-fluorouracil, etoposide, camptothecin, actinomycin-D, mitomycin C, or more preferably, cisplatin. The DNA damaging agent may be prepared and used as a combined therapeutic composition, or kit, by combining it with a p202 composition, as described above.

Agents that directly cross-link polynucleotides, specifically DNA, are envisaged and are shown herein, to eventuate DNA damage leading to a synergistic antineoplastic combination. Agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamnil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of polynucleotide precursors and subunits also lead to DNA damage. As such a number of polynucleotide precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of DNA damage, or the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventor proposes that the regional delivery of p202 compositions to patients with tumors will be a very efficient method for delivering a therapeutically effective gene to counteract the clinical disease. Similarly, the chemo- or radiotherapy may be directed to a particular, affected region of the subject's body. Alternatively, systemic delivery of the p202 or the DNA damaging agent may be appropriate in certain circumstances, for example, where extensive metastasis has occurred.

Cytokine therapy also has proven to be an effective partner for combined therapeutic regimens. Various cytokines may be employed in such combined approaches. Examples of cytokines include IL-1α IL-1β, IL-2, IL-3, IL-4, IL-5, IL-6, IL-7, IL-8, IL-9, IL-10, IL-11, IL-12, IL-13, TGF-β, GM-CSF, M-CSF, G-CSF, TNF-α, TNF-β, LAF, TCGF, BCGF, TRF, BAF, BDG, MP, LIF, OSM, TMF, PDGF, INF-α, IFN-β, IFN-γ. Cytokines are administered according to standard regimens, as described below, consistent with clinical indications such as the condition of the patient and relative toxicity of the cytokine.

A number of polypeptides are known to induce apoptosis and may be used in the combination therapies of the present invention. In one embodiment, the combination therapy is the use of p202 with a polypeptide form the tumor necrosis factor ("TNF") family. In a preferred embodiment, the TNF polypeptide is TNFα. Other polypeptide inducers of apoptosis that may be used in the present invention include, but are not limited to, p53, Bax, Bak, Bcl-x, Bad, Bim, Bik, Bid, Harakiri, Ad E1B, Bad and ICE-CED3 proteases.

F. Pharmaceutical Compositions and Routes of Administration

Compositions of the present invention will have an effective amount of a gene for therapeutic administration in combination with an effective amount of a compound (second agent) that is an anti-cancer agent as exemplified above. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifimgal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

The expression vectors and delivery vehicles of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The vectors of the present invention are advantageously administered in the form of injectable compositions either as liquid solutions or suspensions; solid forms suitable for solution in, or suspension in, liquid prior to injection also may be prepared. These preparations also may be emulsified. A typical compositions for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as theyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

All the essential materials and reagents required for inhibiting tumor cell proliferation may be assembled together in a kit. When the components of the kit are provided in one or more liquid solutions, the liquid solution preferably is an aqueous solution, with a sterile aqueous solution being particularly preferred.

For in vivo use, a chemotherapeutic agent may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the gene therapy and/or the chemotherapeutic drug.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

The active compounds of the present invention will often be formulated for parenteral administration, e.g., formulated for injection via the intravenous, intramuscular, subcutaneous, or even intraperitoneal routes. The preparation of an aqueous composition that contains a second agent(s) as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infuision, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

Targeting of cancerous tissues may be accomplished in any one of a variety of ways. Plasmid vectors and retroviral vectors, adenovirus vectors, and other viral vectors all present means by which to target human cancers. The inventors anticipate particular success for the use of liposomes to target p202 genes to cancer cells. For example, DNA encoding p202 may be complexed with liposomes in the manner described above, and this DNA/liposome complex injected into patients with certain forms of cancer, such as sbreast cancer, intravenous injection can be used to direct the gene to all cell. Directly injecting the liposome complex into the proximity of a cancer can also provide for targeting of the complex with some forms of cancer. For example, cancers of the ovary can be targeted by injecting the liposome mixture directly into the peritoneal cavity of patients with ovarian cancer. Of course, the potential for liposomes that are selectively taken up by a population of cancerous cells exists, and such liposomes will also be useful for targeting the gene.

Those of skill in the art will recognize that the best treatment regimens for using p202 to suppress tumors can be straightforwardly determined. This is not a question of experimentation, but rather one of optimization, which is routinely conducted in the medical arts. The in vivo studies in nude mice provide a starting point from which to begin to optimize the dosage and delivery regimes. The frequency of injection will initially be once a wk, as was done some mice studies. However, this frequency might be optimally adjusted from one day to every two weeks to monthly, depending upon the results obtained from the initial clinical trials and the needs of a particular patient. Human dosage amounts can initially be determined by extrapolating from the amount of p202 used in mice. In certain embodiments it is envisioned that the dosage may vary from between about 1 $\mu$g p202 DNA/Kg body weight to about 5000 $\mu$g p202 DNA/Kg body weight; or from about 5 $\mu$g/Kg body weight to about 4000 $\mu$g/Kg body weight or from about 10 $\mu$g/Kg body weight to about 3000 $\mu$g/Kg body weight; or from about 50 $\mu$g/Kg body weight to about 2000 $\mu$g/Kg body weight; or from about 100 $\mu$g/Kg body weight to about 1000 $\mu$g/Kg body weight; or from about 150 $\mu$g/Kg body weight to about 500 $\mu$g/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 $\mu$g/Kg body weight. In other embodiments, it is envisaged that higher does may be used, such doses may be in the range of about 5 mg p202 DNA/Kg body to about 20 mg p202 DNA/ Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

G. Transgenic Animals/Knockout Animals

In one embodiment of the invention, transgenic animals are produced which contain a functional transgene encoding a functional p202 polypeptide or variants thereof. Transgenic animals expressing p202 transgenes, recombinant cell lines derived from such animals and transgenic embryos may be useful in methods for screening for and identifying agents that induce or repress function of p202. Transgenic animals of the present invention also can be used as models for studying indications such as cancers.

In one embodiment of the invention, a p202 transgene is introduced into a non-human host to produce a transgenic animal expressing a human or murine p202 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous p202 by homologous recombination between the transgene and the endogenous gene; or the endogenous gene may be eliminated by deletion as in the preparation of "knock-out" animals. Typically, a p202 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress p202 or express a mutant form of the polypeptide. Alternatively, the absence of a p202 in "knock-out" mice permits the study of the effects that loss of p202 protein has on a cell in vivo. Knock-out mice also provide a model for the development of p202-related cancers.

As noted above, transgenic animals and cell lines derived from such animals may find use in certain testing experiments. In this regard, transgenic animals and cell lines capable of expressing wild-type or mutant p202 may be exposed to test substances. These test substances can be screened for the ability to enhance wild-type p202 expression and or function or impair the expression or function of mutant p202.

EXAMPLES

The following examples are included to demonstrate preferred embodiments of the invention. It should be appreciated by those of skill in the art that the techniques disclosed in the examples which follow represent techniques discovered by the inventor to fimction well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Material and Methods

Plasmids p202 cDNA, SEQ ID No 1 and Choubey et al., 1989, was cloned into the BamH1 site of the plasmid pCMV to generate pCMV-202 (Choubey et al., 1996). The control plasmid pcDNA3, was obtained from Invitrogen (San Diego, Calif.).

Cell Culture

Human breast cancer cell lines MDA-MB-453 and MCF-7, human prostate cancer cell lines PC-3 and DU145, and human pancreatic cancer cell lines panc-1, Capan-1, BXPC-1, ASPC-1, and CFPAC-1 were obtained were obtained from the American Type Culture Collection (ATCC). The human ovarian cancer cell line SKOV3-IP1 were obtained from Dr. Janet Price (Department of Cancer Biology, M. D. Anderson Cancer Center). Cells were maintained in Dulbecco's modified Eagle's medium (DMEM)/F-12 (HyClone Laboratories, Inc. (Logan Utah) supplemented with 10% (v/v) fetal bovine serum.

Irradiation of Cells

Cells were irradiated using an Irradiator $^{137}$Cs source as a dose of 3.7 Gy/min for a total of 40 Gy.

Transfection, Colony Forming Assay and Establishment of Stable Cell Lines

Cells were transfected with a p202 expression vector under the CMV promoter (CMV-p202), (Choubey et al., 1996) or the control vector pcDNA3 (Invitrogen, San Diego, Calif.) using lipofectin (GIBCO) as described in the manufacture's protocol. Briefly, cells ($5\times10^5$) were plated in 60-mm dish 24 h before transfection. Transfection was done in serum free medium for 4–5 h and then the transfected cells were grown in fresh complete medium. Forty-eight h later, cells were split into 100-mm dishes and grown in the medium containing 500 $\mu$g/ml G418 (Geneticin, GIBCO BRL). After 3 weeks of G418 selection, the drug resistant colonies (greater than 2 mm in diameter) were stained with crystal violet and counted. To isolate p202-expressing stable cell lines, G418-resistant colonies were randomly cloned and analyzed for p202 expression by western blot. The G418-resistant colonies from pcDNA-3 transfections were pooled as controls.

Western Blot p202 transfected cells were lysed at 4° C. in a lysis buffer containing 20 mM sodium phosphate (pH 7.4), 150 mM NaCl, 1% Triton X-100, 5 mM phenylmethylsulfonyl fluoride, 1% aprotinin, 10 $\mu$g/ml leupeptin, 100 mM sodium fluoride, and 2 mM $Na_3VO_4$. Aliquot of the cell lysate (50 $\mu$g) were separated by sodium sulfate-polyacrylamide gel electrophoresis (SDS-PAGE) (10% polyacrylamide) and transferred to nitrocellulose membranes. The membranes were blocked in TBST (Tris-buffered saline with Tween-20) with 5% nonfat milk for lh and then incubated with anti-p202 antibody (rabbit polyclonal (Choubey and Lengyel, 1993), provided by Dr. Choubey) at 4° C. overnight. The peroxidase-conjugated goat anti-rabbit antibody was used as the secondary antibody and the blots were visualized by the Enhanced Chemiluminescence (ECL) Detection System (Amersham).

Growth Rate Analysis

CyQuant assay. The quantity of both RNA and DNA was measured by using a CyQuant Cell Proliferation Assay kit (Molecular Probes, Eugene, Oreg.). The cells were seeded in four 96-well plates (for four-day measurement). Every 24 h, a plate was removed from the incubator, aspirated, and stored in a –80° C. freezer. After all the plates were collected, a lysis buffer containing the CyQuant dye was added to the wells and the plates were read on a Cytofluor 2350 Fluorescence Measurement System (Millipore, Bedford, Mass.).

For direct cell counting, cells growing in logarithmic phase in DMEM/F12 media supplemented with 10% fetal bovine serum were trypsinized, counted, and seeded in 60 mm culture dishes at 50,000 cell per dish. At 24 h intervals the cells were trypsinized and an aliquot was counted on a Coulter Counter ZM (Coulter Corporation, Miami, Fla.). All counts were done in triplicate.

MTT assay. Cells were plated in triplicate in 96 well plates ($5\times10^3$ cells per well). At each time point, 25 $\mu$l of MTT (3, (4,5-dimethylthiazol-2-yl) 2,5-diphenyltetrazolium bromide, 5 mg/ml) was added and incubated for two h at 37° C. followed by addition of 100 $\mu$l of extraction buffer (20%

SDS in 50% dimethyl formamide, pH 4.7). After an overnight incubation at 37° C. the plates were read at 570 nm on a Dynatech MR 5000-plate reader (Dynatech Laboratories, Chantilly, Va.).

[$^3$H]-Thymidine Incorporation Assay

Cells were plated (1×10$^3$ cells per well) in 96-well plates and incubated with 1 $\mu$Ci of [$^3$H]-Thymidine for 8–12 h. The cells were then trypsinized and immobilized on the Whatman glass fiber filters using a cell harvester. The radioactivity of the cells was determined using a scintillation counter (Beckman). Each measurement represents an average of quadruplicates.

Transformation Soft Agar Assay

Cells 1×10$^4$) were mixed at 37° C. with 0.5% agarose (Sea Plaque, low gelling temperature, FMC Bioproducts, Rockland, Me.) in complete media. They were allowed to solidify at 4° C. for 15 min over a previously cast 1% agarose layer with complete media in 6-well plates. After three weeks of incubation, 200 $\mu$l (1 mg/ml) of p-iodonitrotetrazolium violet was added and incubated for an additional 24 h. Colonies were counted and photographed using a Nikon Diaphot-TMD microscope at 40×magnification.

Tumorigenicity assay

Female athymic nude mice (nu/nu), 4–5 weeks old, were used in this ex vivo study. MCF-7 cells were grown at 80% confluence in 100-mm dishes before they were transfected with CMV-p202 (10 $\mu$g) with polyethylenimine (PEI) (Boussif et al., 1995). Twenty-four h after transfection, cells (3×10$^6$) were harvested in 0.2 ml of PBS and injected into the mouse mammary fat pads. 17-$\beta$-estradiol pellets (0.72 mg/pellet, 60-day release, Innovative Research of America) were implanted subcutaneously into the mice one day before cell injection.

For tumorigenicity assay in p202-expressing PC-3 cells, mice were injected subcutaneously with 1×10$^5$ PC-3-p202 cells or control cells in each of the two sides of the abdomen. The size of the tumors was measured with a caliper every wk and the tumor volume was calculated using a formula: Vol.=½×S$^2$×L, where S=the short length of the tumor, and L=the long length of the tumor in cm.

Cell Viability Assay

MDA-MB-453 and 453-p202 cells were plated in 6-well plates 1×10$^5$ cells per well). 0.5 $\mu$g of pCMV-Luciferase and 0.5 $\mu$g of pCMV-$\beta$-galactosidase were complexed with LPD1 (a cationic lipid provided by Dr. Leaf Huang) before transfected into the cells. Twenty-four h after transfection, cells were trypsinized and divided into two groups: one half of the cells were grown in serum-free medium for 48 h, and the other half were maintained in complete medium. Cytoplasmic extract isolation and luciferase assay were done according to the protocol provided by the manufacturer (Promega). The cell viability was measured by the luciferase activity that was subsequently corrected by $\beta$-galactosidase activity in the same sample to normalize the transfection efficiency.

Apoptosis Analysis by Flow Cytometry

Cells were treated with TNF-$\alpha$ (20 ng/ml) or serum starvation. Forty-eight h later, cells were harvested and kept in cold PBS. An aliquot of cells (4×10$^5$) was spun down and fixed in 1 ml of 75% ethanol at 4° C. overnight. The fixed cells were washed twice with PBS and suspended in 1 ml of PBS (with 0.5% Tween-20) containing 10 $\mu$g of RNase and 10 $\mu$g of propidium iodide and kept at 4° C. The stained cells were analyzed by a FACScan flow cytometer (Becton Dickinson).

Gel-shift Assay

Nuclear extract isolation: cells were treated either with TNF-$\alpha$ (20 ng/ml) for 30 min or serum starvation for 24 h before the cell extracts were isolated. Cells were scrapped into 1.5 ml of cold PBS, pelleted, and resuspended in 100 $\mu$l of cold buffer A (10 mM HEPES-KOH, pH 7.9, 1.5 mM MgCl$_2$, 10 mnM KCl, 0.5 mM dithiothreitol, 0.2 mM phenylmethylsulfonyl fluoride) by flicking the tube. Cells were allowed to swell on ice for 10 min, and then vortexed briefly. Samples were centrifuged using a microfuge for 10 sec, and the supernatant was discarded. The pellet was resuspended in 20–100 $\mu$l of cold buffer C (20 mM HEPES-KOH, pH 7.9, 25% glycerol, 420 mM NaCl, 1.5 mM MgCl$_2$, 0.2 mM EDTA, 0.5 mM dithiothreitol, 0.2 mM phenylmethylsulfonyl fluoride) and incubated on ice for 20 min. Cellular debris was removed by centrifugation for 2 min at 4° C., and the supernatant containing DNA-binding proteins was stored at –70° C. For the mobility-shift assay, nuclear extract (5 $\mu$g) was incubated with 1$\mu$g of poly (dI-dC) (Pharmacia Biotech Inc.) on ice for 20 min, and a $^{32}$P-labeled double-stranded oligonucleotide containing the $\kappa$B site from the human immunodeficiency virus was added. The protein/DNA binding was carried out at room temperature for 20 min. The resulting NF-$\kappa$B/DNA complexes were visualized using a non-denaturing polyacrylamide gel (4%) electrophoresis followed by autoradiography. The mutant $\kappa$B competitor is a wild type oligonucleotide containing mutations in the NF-$\kappa$B binding site.

Immunoprecipitation and Immunoblotting

MDA-MB-453 (453) and 453-p202 cells were treated with TNF-$\alpha$ (20 ng/ml) for 30 min. Cells with or without TNF-$\alpha$ treatment were extracted in RIPA-B lysis buffer (20 mM sodium phosphate (pH 7.4), 150 mM NaCl, 1% Triton X-100, 5 mM phenylmethylsulfonyl fluoride, 1% aprotinin, 10 $\mu$g/ml leupeptin, 100 mM sodium fluoride, and 2 mM Na$_3$VO$_4$) on ice. Cell lysates were briefly sonicated and cleared by centrifuge at 4° C. for 5 min. For immunoprecipitation, equivalent aliquots of cell lysates (1 mg of total protein) were incubated with 1 $\mu$g of anti-p65 antibody (Santa Cruz) at 4° C. for 4 h with gentle rotation. 50% slurry of protein A Sepharose beads was added for an addition 1 h. Following three washes in lysis buffer, proteins bound to the beads were eluted by boiling in SDS gel sample buffer, separated by SDS-PAGE, and transferred to a nitrocellulose membrane. The immunoblotting with anti-p202 antibody was performed as previously described (Yan et al., 1999).

Luciferase Reporter Assay

Cytoplasmic extract isolation and luciferase assay were done according to the protocol provided by the manufacturer (Promega). For $\kappa$-luc and Rel-A co-transfection, total 3.3 $\mu$g of DNA (0.3 $\mu$g $\kappa$B-luc with or without 1.2 $\mu$g p65Rel-A and/or 1.8 $\mu$g CMV-p202; and an appropriate amount of pSV-neo used as stuffer) was complexed with lipofectin (GIBCO) and transfected into 453 cells (1.5×10$^5$). Forty-eight h after transfection, cells were harvested and assayed for the luciferase activity. To normalize the transfection efficiency, a parallel transfection was done using LTR-Luciferase vector alone, in which LTR does not contain NF-$\kappa$B binding site.

Example 2 p202 Expression Inhibits Cell Growth in Breast Cancer Cells

Figure 2A:
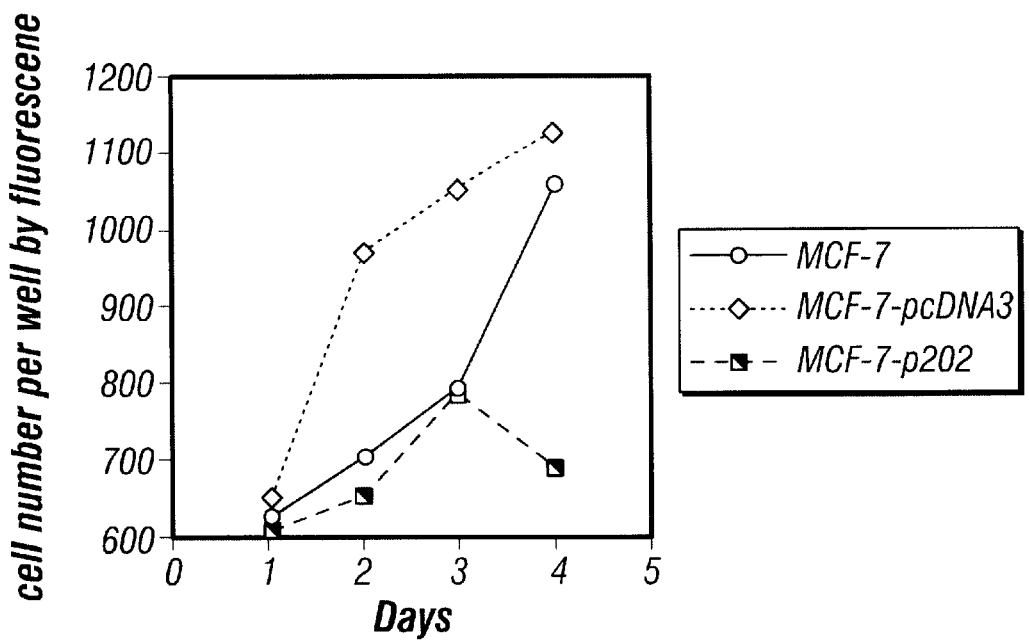
FIGS. 2A, 2B, 2C, 2D, 2E and 2F. Expression of p202 inhibits the proliferation of MDA-MB453 and MCF-7 breast cancer cells.
Figure 2B:
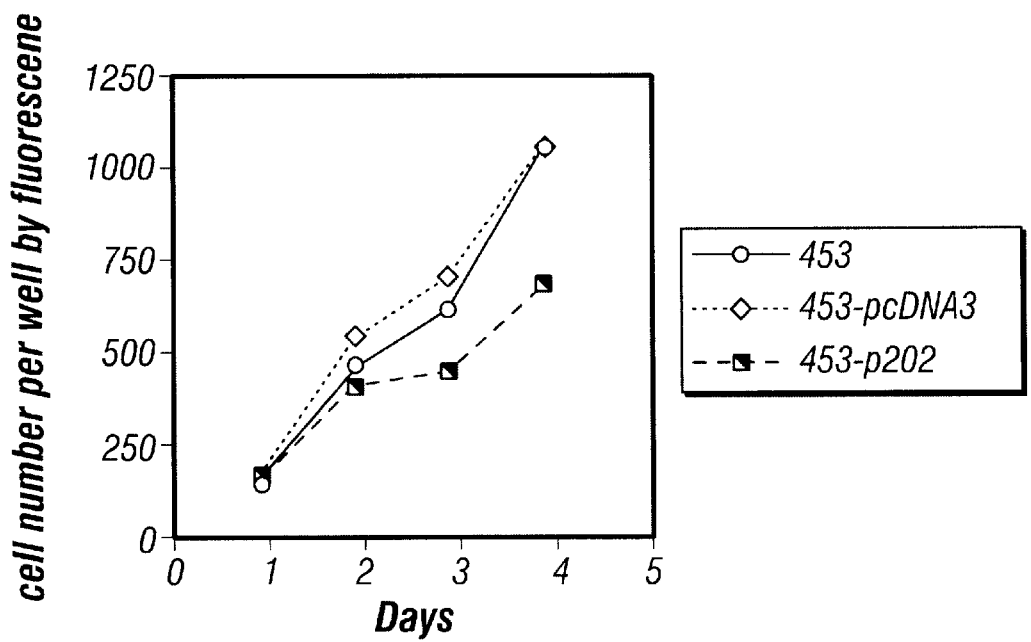
Figure 2C:
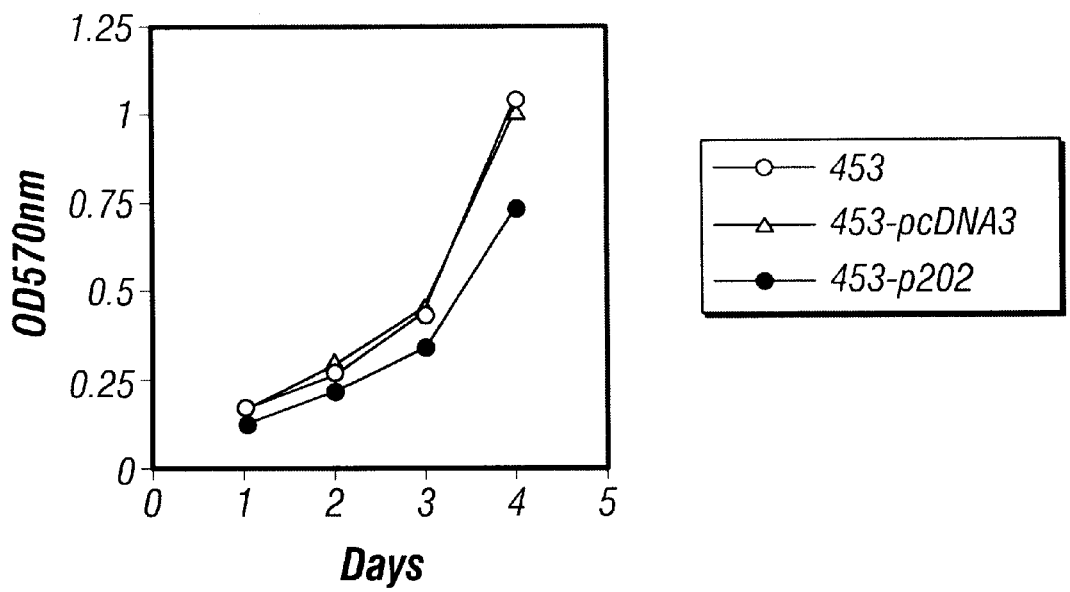
Figure 2D:
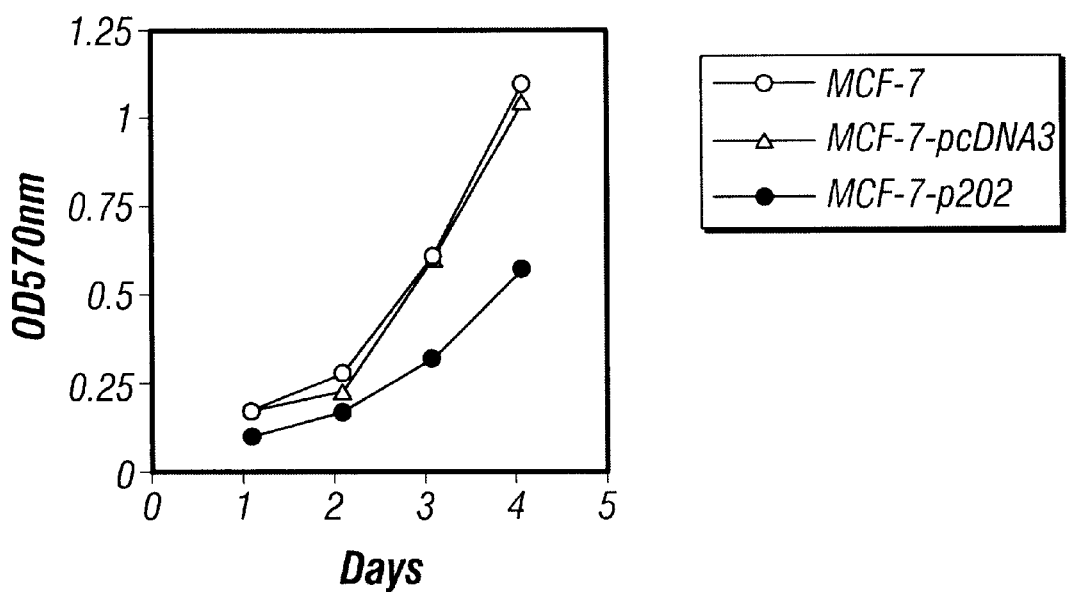
Figure 2E:
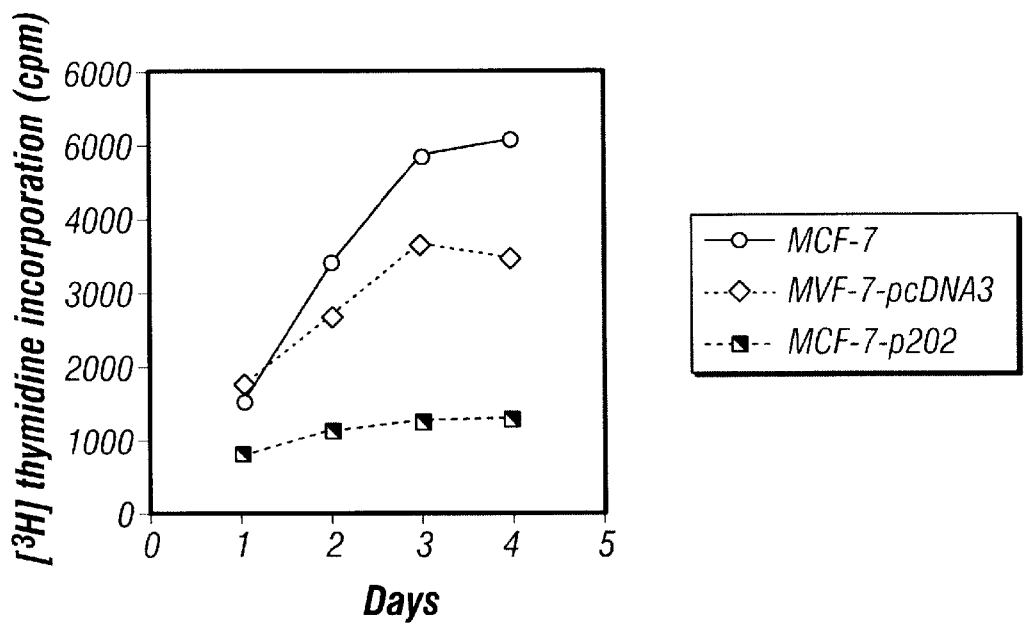
Figure 2F:
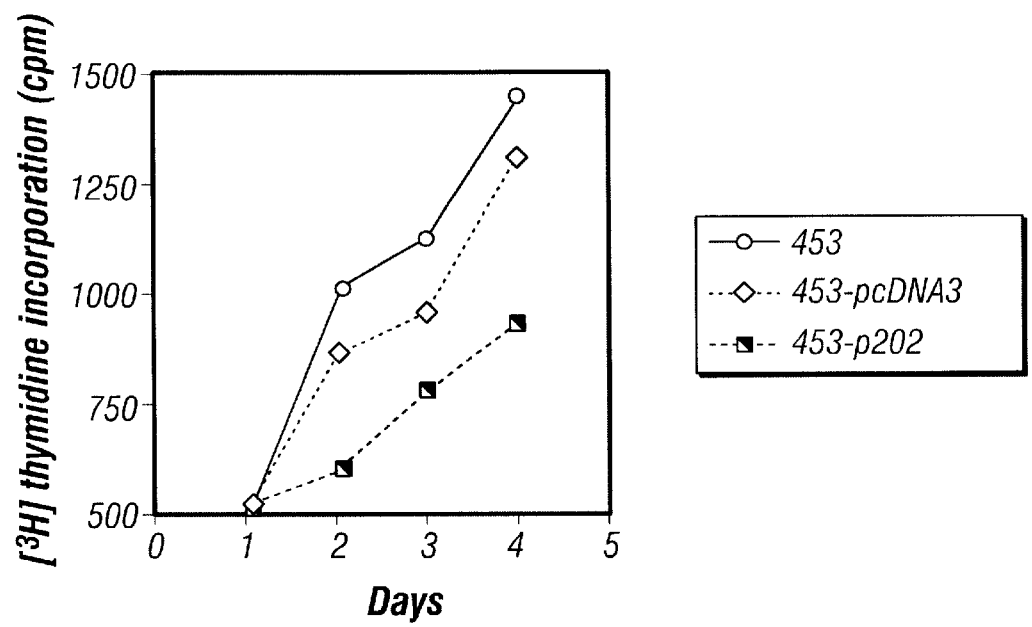

The growth inhibitory effect of p202 on breast cancer cells was investigated by transfection of a p202 expression plasmid driven by CMV promoter (CMV-p202) or a control vector (pcDNA3) into two human breast cancer cell lines, MDA-MB-453 (453) and MCF-7 in a colony forming assay. Since both plasmids contain a neomycin resistant gene, the number of G418-resistant colony by crystal violet staining was scored after three weeks of G418 selection. There was a dramatic reduction in the number of G418-resistant colony in p202 transfected cells as compared with that of the control transfection, pcDNA3 (FIG. 1). These results suggest that p202 expression may has an anti-proliferation and/or pro-apoptosis effect on these cells. To further characterize the biological effects of p202 expression on breast cancer cells, several lines of p202-expressing stable clones were isolated. Using western blot with a p202-specific antibody (Choubey and Lengyel, 1993), the inventors were able to identify one p202-expressing stable clone (out of 20) from each cell line, i.e. MDA-MB-453-p202 (453-p202), and MCF-7-p202. However, the low frequency of p202-expressing clones is expected according to the previous observations (Yan et al., 1999). To assess the growth properties of these p202-expressing cells, the growth curves between the p202 stable lines and the control cell lines were measured. The p202-expressing cells showed a somewhat reduced growth rate after three days as compared with their respective control cell lines, 453 and MCF-7 (FIGS. 2A–2D). The reduced growth rate could be the net result of anti-replication and/or apoptosis caused by p202 expression. However, no apoptosis was observed in either p202 transfectant cell lines under the normal growth condition determined by FACS analysis. This result suggested that the p202-mediated growth retardation might be due to a slower cell replication rate in these cells. This prediction is supported by the observation that the p202-expressing cells (453-p202 and MCF-7-p202) exhibited a slower DNA synthesis rate than the control cell lines as measured by [$^3$H]-thymidine incorporation assay (FIGS. 2E, 2F). These data strongly indicate that p202 could function as a growth inhibitor in breast cancer cells.

Example 3 p202 Expression Inhibits Transformation Phenotype in Breast Cancer Cells

Figure 3:
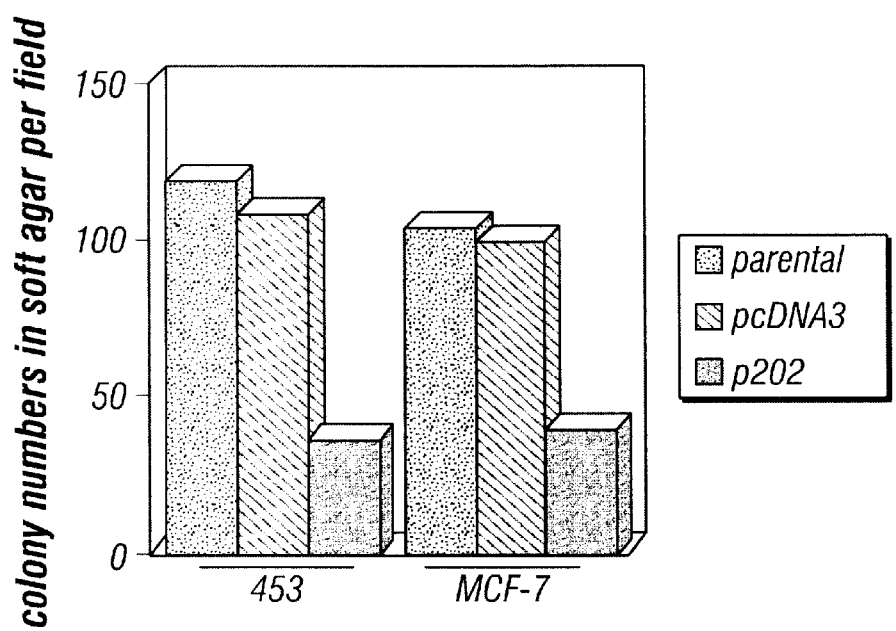
FIG. 3. p202 inhibits the transformation phenotype of breast cancer cells. p202 transfectants and control cells were plated in 6-well plates at $1 \times 10^4$ cells per well in semi-solid medium, containing 0.5% agarose over a 1% agarose layer. After three weeks, the colonies were stained by p-iodonitrotetrazolium violet and scored under a microscope at 40× magnification. p202 transfectants were incubated for three more weeks and re-scored. The bar diagram shows the number of colonies formed in soft agar per microscopic field, which represents the average of five random field from each cell line.

The ability of p202 expression in breast cancer cells to suppress the transformation phenotype defined by the ability of anchorage-independent growth in soft agar was examined. As shown in FIG. 3, both 453-p202 and MCF-7-p202 exhibited more than 60% reduction (after three weeks of incubation) in the colony number than those of the control cell lines, i.e., parental and pcDNA3 transfectant. A prolonged (six weeks) incubation of the same plates did not yield more colonies. This data suggested that the observed reduction of colony number in soft agar may not be attributed totally to the reduced growth rate of these cells (FIGS. 2C–F), but rather it may represent a real loss of the transformation phenotype in these p202-expressing cells.

Example 4

P202 Expression Inhibits Tumorigenicity of Breast Cancer Cells In Vivo

Figure 4:
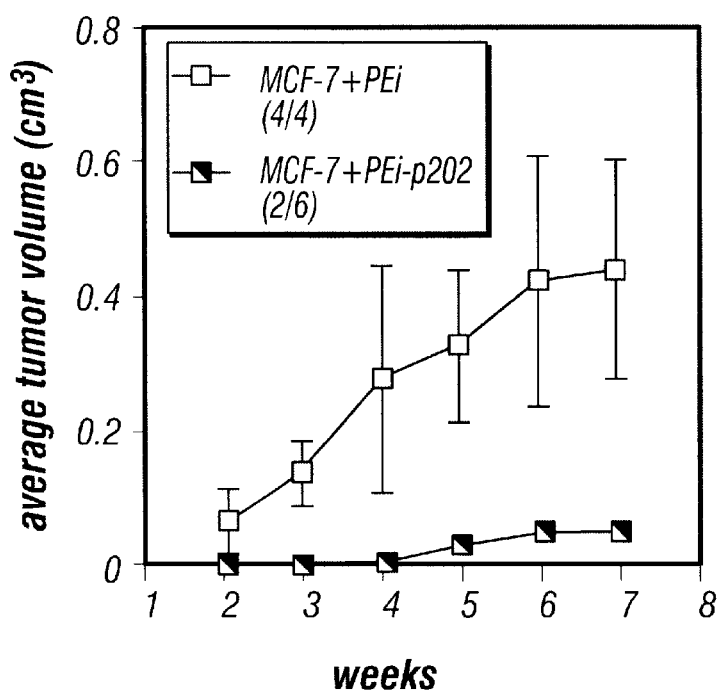
FIG. 4. p202 inhibits the tumorigenicity of breast cancer cells. MCF-7 cells were grown at 80% confluence in 100-mm dishes and transfected with 10 μg of p202 expression vector using polyethylenimine (PEI). After transfection the cells were grown for 24 h, harvested and $3 \times 10^6$ of p202 transfected cells or PEI mock-transfected cells were injected into the mammary fat pad of female nude mice. 17-β-estradiol pellets were implanted subcutaneously into the mice one day before cell inoculation. Tumor formation was monitored every wk and the tumor volume was calculated using the formula: $0.5 \times S^2 \times L$, where S=the short length of the tumor, L=the long length of the tumor.

To determine whether the loss of transformation phenotype of p202-expressing cells observed in vitro may also predict a reduced tumorigenicity of these cells in vivo, a tumorigenicity assay in an orthotopic breast cancer mouse model was performed. Since MCF-7 cells can form tumors in mice implanted with estrogen pellets (Gottardis et al., 1988), the inventors used a MCF-7 mouse model to test the above hypothesis. CMV-p202/PEI or PEI alone was transfected into MCF-7 cells and then the transfected cells were injected into the mammary fat pads of these estrogen-supplemented nude mice. The p202 transfection caused a drastic reduction of tumorigenesis in MCF-7 cells as compared with that of the mock transfection (PEI alone) (FIG. 4). This result showed, that p202 expression is associated with an anti-tumor activity in animals. Interestingly, the breast cancer cell lines used in this study confer either estrogen receptor (ER) negative (MDA-MB-453) or ER positive (MCF-7) status. Therefore, the p202-mediated anti-growth and anti-tumor activities in breast cancer cells appear to be independent of ER status. This observation is consistent to the finding that the IFN-mediated growth inhibition in breast cancer cells was also irrespective of their ER status (Coradini et al., 1994; Coradini et al., 1994a).

Example 5 p202 Expression Sensitizes Breast Cancer Cells to Apoptosis

Figure 5A:
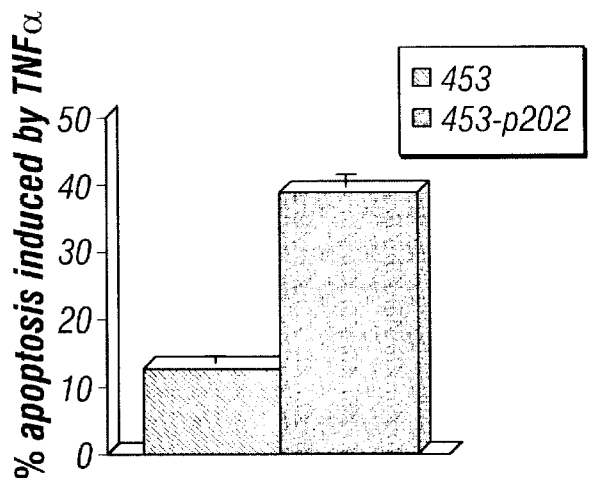
FIGS. 5A, 5B and 5C. p202 sensitizes MDA-MB-453 breast cancer cells to apoptosis induced by TNF-α or serum depletion.
Figure 5B:
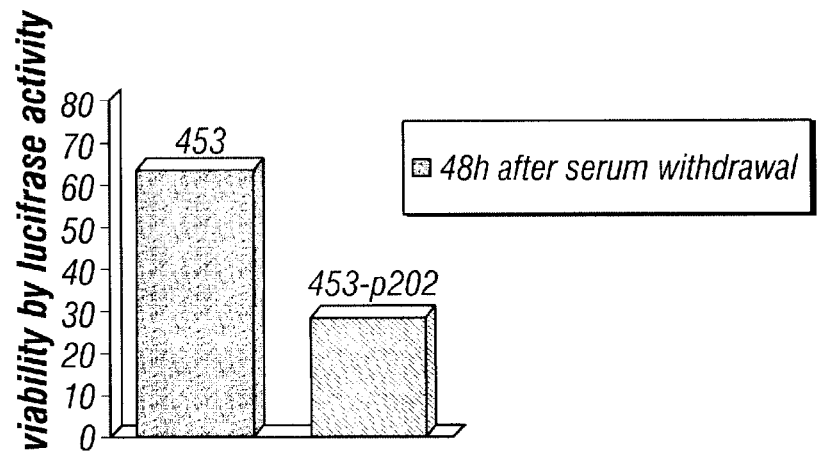
Figure 5C:
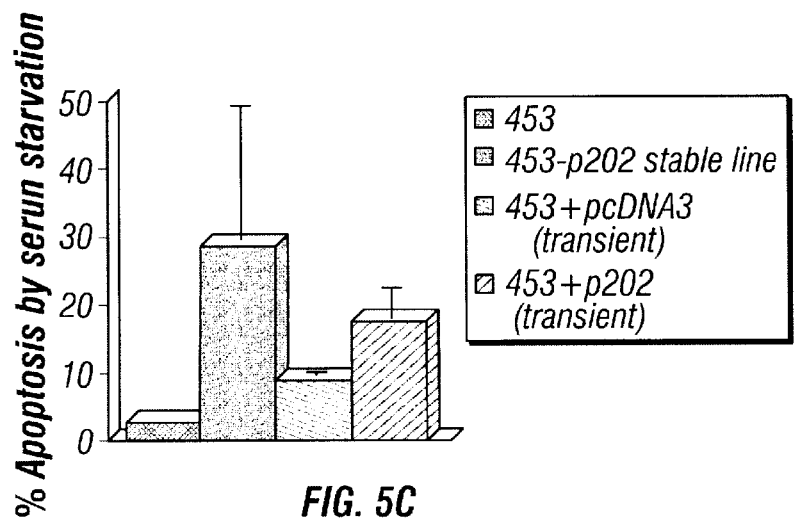

In an attempt to identify therapeutic agents that may cooperate with p202 to synergize the anti-tumor effect on breast cancer cells, it was found that the p202-expressing cells, e.g., 453-p202, were more susceptible to TNF-$\alpha$ and serum withdrawal-induced apoptosis (FIG. 5) than the parental 453 cells. In the presence of TNF-$\alpha$, the inventors observed a three-fold higher apoptosis in 453-p202 cells than that in the parental 453 cells (FIG. 5A). This result suggests that p202 expression might sensitize MDA-MB-453 cells to TNF$\alpha$-induced apoptosis. In addition, it is interesting to find that p202 expression can also sensitize breast cancer cells to serum withdrawal-mediated apoptosis. A transient transfection assay using luciferase expression vector as a relatively more sensitive, albeit an indirect, indicator to estimate the number of viable cells was employed. The luciferase activity was assayed after the transfected cells were grown in a serum free condition for 48 h. FIG. 5B shows an approximately 35% less viable cells in 453-p202 than that of 453 cells. It is likely that this apparent difference in viability may be due to the p202-associated apoptosis in these cells. To test that possibility, a direct measurement of the number of apoptotic cells (in %) was taken by subjecting the samples shown in FIG. 4B to FACS analysis. A 10-fold induction of apoptosis in 453-p202 as compared with that in 453 cells was observed (FIG. 5C). Thus, these results support the idea that p202 could also sensitize 453 cells to serum depletion-induced apoptosis. To rule out the possibility that the observed difference is due to clonal heterogeneity between the selected clones, it was tested whether a p202-mediated sensitization to serum depletion-induced apoptosis could be observed in the transiently transfected 453 cells. As shown in FIG. 5C that, like 453-p202, the p202-transfected 453 cells appeared to be more sensitive to serum depletion-induced apoptosis than that of the control vector transfection. The apparent smaller difference seen in the transient assay than observed in the selected clones may be due to the limitation of trsfection efficiency. Interestingly, it has been previously shown that an endogenous level of p202 expression was sufficient to prevent a murine fibroblast cell line, AKR-2B, from entering apoptosis when they were grown in medium containing 1% serum (Koul et al., 1998). It is likely that a threshold of p202 expression may exist and that may determine the cell fate in response to serum withdrawal induced apoptosis, also the inventors could not rule out a possible tissue-specific effect of p202 in these experimental systems. In which case, it will be benefit to obtain the specificity for cancer therapy.

Inflammatory cytokines, e.g., TNF family members, can transduce apoptotic signals in certain tumor cells (Sugarman et al., 1985). While some cancer cells are resistant to TNF-α-induced apoptosis, the majority of them could be sensitized to apoptosis in the presence of transcription or translation inhibitors (Kull, Jr. and Cuatrecasas, 1981). The present invention demonstrates that p202 expression can also sensitize breast cancer cells to TNF-α-induced apoptosis. Moreover, it implicates a potential therapeutic application of a combined treatment of TNF-α and p202 gene therapy for breast cancer patients regardless the ER status of their tumnors.

Figure 6A:
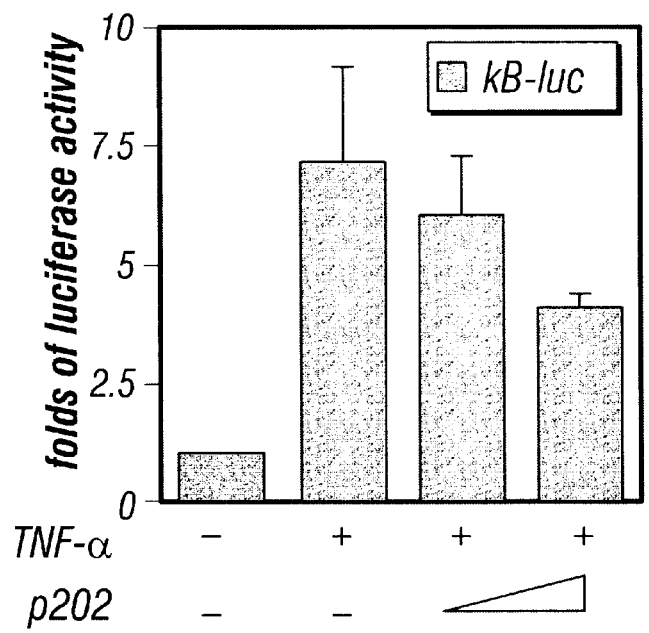
FIGS. 6A, 6B, 6C and 6D. The interaction and inactivation of NF-κB by p202 is responsible for the p202-mediated sensitization to TNF-α induced apoptosis, but not serum starvation induced apoptosis.
Figure 6B:
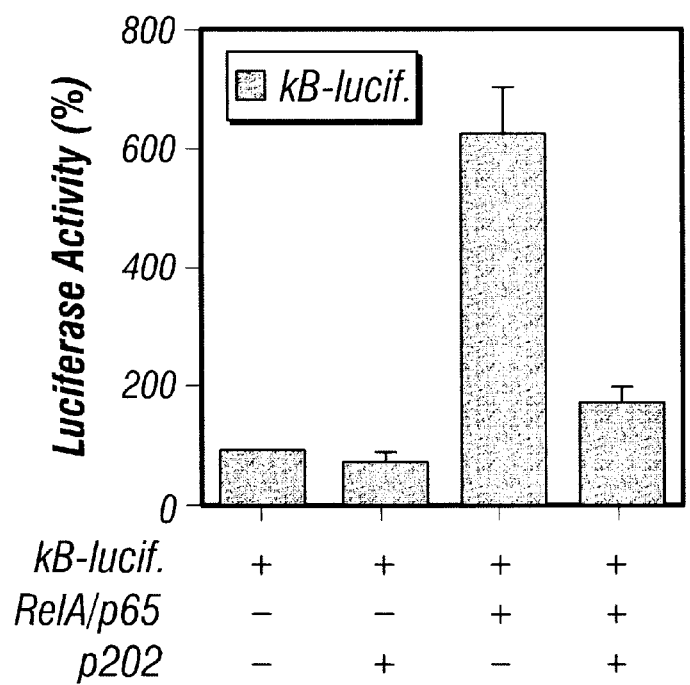
Figure 6C:
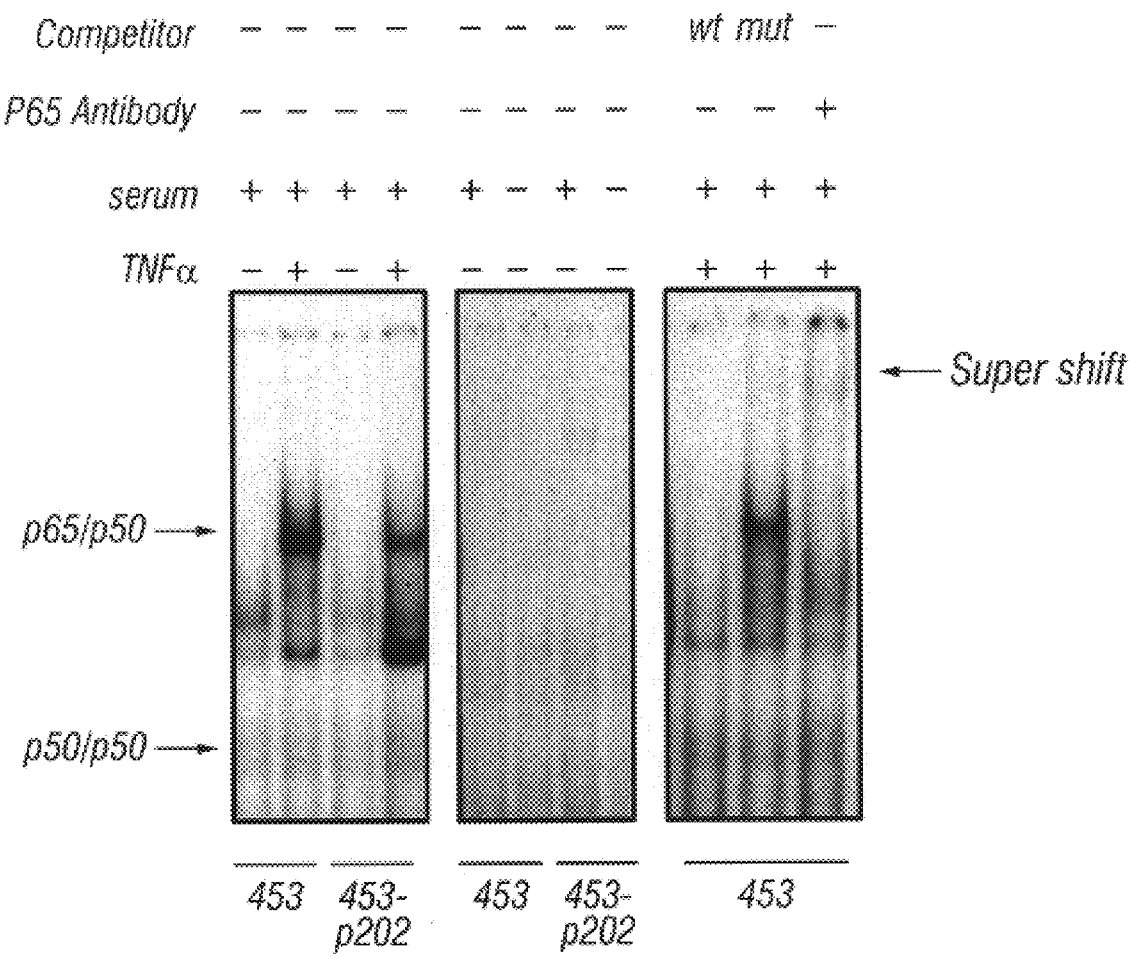
Figure 6D:
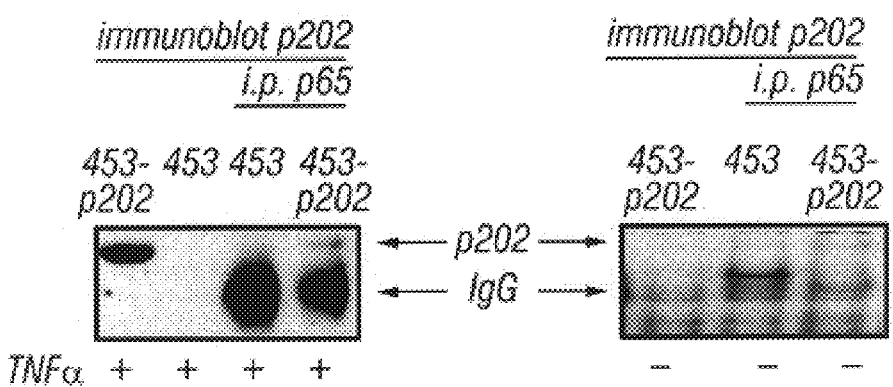

Since NF-κB is known to be an anti-apoptotic molecule that counteracts TNF-α-induced apoptosis (Wang et al., 1996; Beg and Baltimore, 1996; Van Antwerp et al., 1996), the possibility that p202 may enhance TNF-α-induced apoptosis by antagonizing the anti-apoptotic function of NF-κB in the cells was examined. It was first tested whether p202 expression could affect the NF-κB-mediated transcription activation in response to TNF-α treatment. CMV-p202 and a NF-κB-activatable promoter-reporter construct (κB-luc), i.e., an IκB promoter driven luciferase gene, were co-transfected into 453 cells in the response to TNF-α (FIG. 6A). As expected, κ-luc was readily activated in the presence of TNF-α. However, this TNF-α-induced transcription activation could be repressed by p202 in a dose-dependent manner. To test whether p202 acted on NF-κB molecule to elicit such transcription repression, CMV-p202 was co-transfected with Rel-A (a p65 subunit of NF-κB) cDNA expression vector and κB-luc. While p202 expression alone has no effect on κ-luc, it could greatly repress NF-κB (Rel-A)-activated IκB promoter activity (FIG. 6B). These results suggest that the transcription repression of TNF-α-mediated gene expression by p202 may be the cause of inactivating NF-κB molecule by p202. This hypothesis was supported by a subsequent observation that p202 expression was associated with a reduced level of the active NF-κB (p65/p50) molecule. (FIG. 6C, left panel). As expected, the level of active NF-κB was found significantly increased in both the p202-expressing (435-p202) and the parental (453) cells treated with TNF-α. However, the level of activated NF-κB was greatly reduced in 453-p202, and which was concurrent to the appearance of most NF-κB molecules remained in the inactive form (p50/p50, the faster migrating band). Using either a wild type or mutant NF-κB DNA binding sequence as a competitor, it was shown that the DNA/protein complex is indeed NF-κB-specific in that only wild type, but not mutant, sequence could compete with the NF-κB/DNA complex. Moreover, the fact that this complex could be super-shifted in the presence of an anti-p65 antibody (FIG. 6C, right panel) further confirmed the identity of this DNA/protein complex being NF-κB-specific. These data support the idea that p202 expression may impede the formation of active p65/p50 heterodimer resulting in the accumulation of inactive p50/p50 homodimer. That, in turn, represses certain genes whose transcription activation requires ftmctional NF-κB. One possible mechanism, based on the gel-shift result, is that p202 may interact with p65 forming a p202/p65 complex, and which may significantly reduce the concentration of free p65 in p202-expressing cell, rendering most of the NF-κB molecules in the inactive form (p150/p65). This idea was further supported by the observation that p202 was found physically associated with p65. As shown in FIG. 4d, left panel, with TNF-α treatment, p202 could be co-immunoprecipitated with p65 by an anti-p65 antibody using 453-p202 nuclear extract, but not 453 extract. As a control, no detectable p202 was observed in both cell lines without TNF-α treatment (FIG. 6D, right panel). These data strongly indicate that p202 and p65 are physically associated together in the same complex. The p65 protein level was comparable between 453 and 453-p202 cells with TNF-α treatment indicating that p202 does not regulate p65 expression. The above observation supports a scenario that TNF-α-induced NF-κB activation could be antagonized by p202 via a p202/p65 interaction leading to transcription repression of genes requiring NF-κB for expression. Although it has been reported previously that p202 could bind both p50 and p65 in vitro and p50 in vivo (Min et al., 1996), the current data is the first demonstration of an in vivo association between p202 and p65 upon TNF-α stimulation. Taken together, the present results provide a possible mechanism that may account for the p202-mediated sensitization to TNF-α-induced apoptosis in breast cancer cell. The p202/p65 interaction may cause inactivation of NF-κB by interfering the formation of a functionally active p65/p50 heterodimer.

Figure 7:
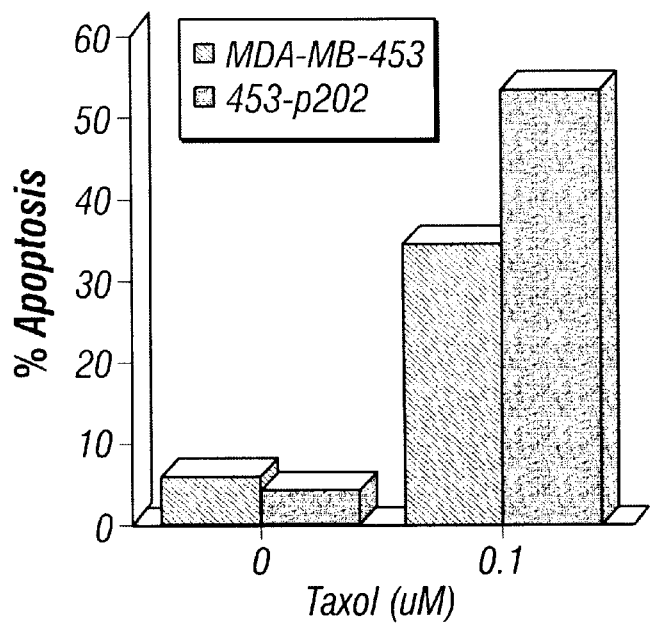
FIG. 7. p202 mediated sensitization to taxol. MDA-MB-453 and 453-p202 cells were plated in 6-well plates and incubated with or without taxol (0.1 μM) for 72 h. Then cells were harvested and analyzed by flow cytometry.
Figure 8:
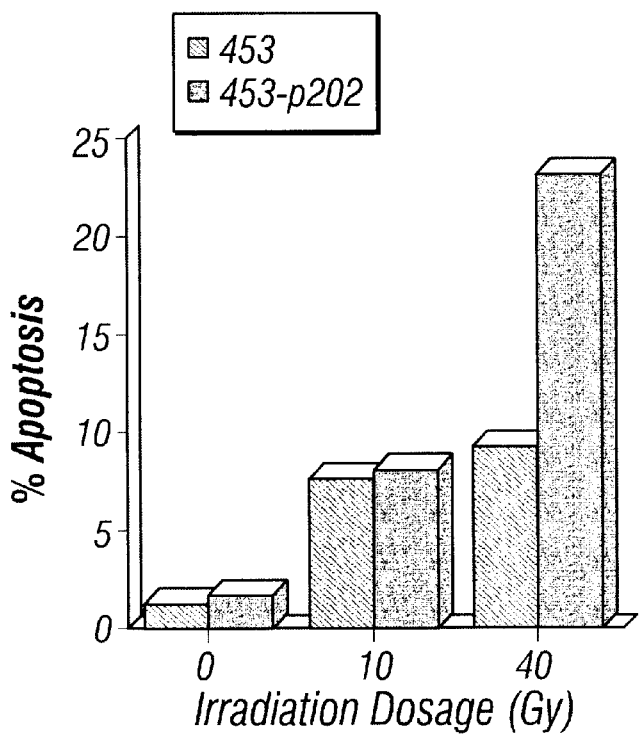
FIG. 8. p202 mediated sensitization γ-irradiation. MDA-MB-453 and 453-p202 cells were exposed to 10 and 40 Gy doses of γ-radiation. Apoptosis was measured 72 h after irradiation by flow cytometry.

Interestingly, the p202 sensitization to serum depletion-induced apoptosis did not appear to be associated with NF-κB inactivation, since there was no detectable level of active NF-κB (p65/p50) observed in cells grown in serum free condition (FIG. 6C, middle panel). Therefore, p202 may sensitize 453 cells to serum depletion-induced apoptosis through a different pathway that is independent of NF-κB inactivation. It has been previously shown that antisense construct of p202 gene was able to induce apoptosis in a murine fibroblast cell line, AKR-2B, when they were grown in medium containing 1% serum (Koul et al., 1998). That result suggests that endogenous level of p202 expression may prevent AKR-2B cells from entering apoptosis. Although a possible tissue-specific effect of p202 in these experimental systems cannot be ruled out, it is likely that a threshold of p202 expression may exist and that would determine the cell fate in response to serum withdrawal-induced apoptosis. In which case, studies are contemplated to determine if different levels of p202 expression, e.g., none-expression or overexpression, may employ the same or a different apoptotic pathway in response to serum depletion.

p202 expression also sensitized MDA-MB-453 cells to apoptosis induced by chemotherapeutic agents. FIG. 7 shows increased taxol-induced apoptosis. Taxol (paclitaxel) is a major clinically used chemotherapeutic agent used against breast cancer. FIG. 8 shows increased irradiation-induced apoptosis when cells were exposed to a dosages of 10 and 40 Gy of γ-radiation. Ionizing radiation ("IR") therapy is an important modality for treatment of local and regional tumors, but it is limited by development of radioresistance in tumor cells. More specifically, radioresistance of tumor cells has been linked with resistance to IR-induced apoptosis. The present invention indicates that p202 may be used to counter the radioresistance of tumor cells.

Example 6 p202 Expression Inhibits Cell Growth in Human Prostate Cancer Cells

A p202 cDNA expression plasmid (CMV-p202) (Choubey et al., 1996) was transfected into PC-3 and DU145. After 3 weeks of G418 selection, the drug-resistant colonies were scored by crystal violet staining. A dramatic reduction, i.e. more than 90% reduction (Table 4), in the number of G418-resistant colonies was observed in both cell lines transfected with CMV-p202 (p202) as compared to the pcDNA3 vector control.

It is possible that the reduction of colony numbers in p202-transfected prostate cancer cells may be caused by the p202-mediated growth retardation and/or apoptosis. To examine these possible mechanisms and to characterize the function of p202, the p202-expressing stable cell lines were isolated. For PC-3, out of twenty randomly selected p202-transfected clones, four clones that express p202 protein by western blot with a polyclonal antibody against p202 were identified (Coubey and Lengyel, 1993): a modest expressor, p202-1, and three high expressors, p202-2, -3, and -4 (Table 4). The control cell lines, PC-3, and the pooled PC-3 colonies transfected with pcDNA3 vector (pcDNA3-pooled), have no detectable endogenous level of p202 protein. As expected, the p202-pooled showed little but detectable p202 protein expression. The positive and negative controls were lysates isolated from ARK-2B cells treated with (+) or without (−) IFN-α, respectively. (Coubey and Lengyel, 1993). It has been previously shown that the p202 antibody also recognizes a 68 kd nonspecific protein which can be used as an internal control for normalizing the sample loading. (Coubey and Lengyel, 1993).

Isolation the p202-expressing DU145 clones was attempted. However, out of twenty G418-resistant colonies screened, none expressed p202 protein (Table 4). It is possible that DU145 cells may be more sensitive to the p202 expression than PC-3 cells since DU145 cells were more sensitive to the IFN-α-induced growth inhibition than PC-3 cells. (Sokoloff et al., 1996).

Figure 9A:
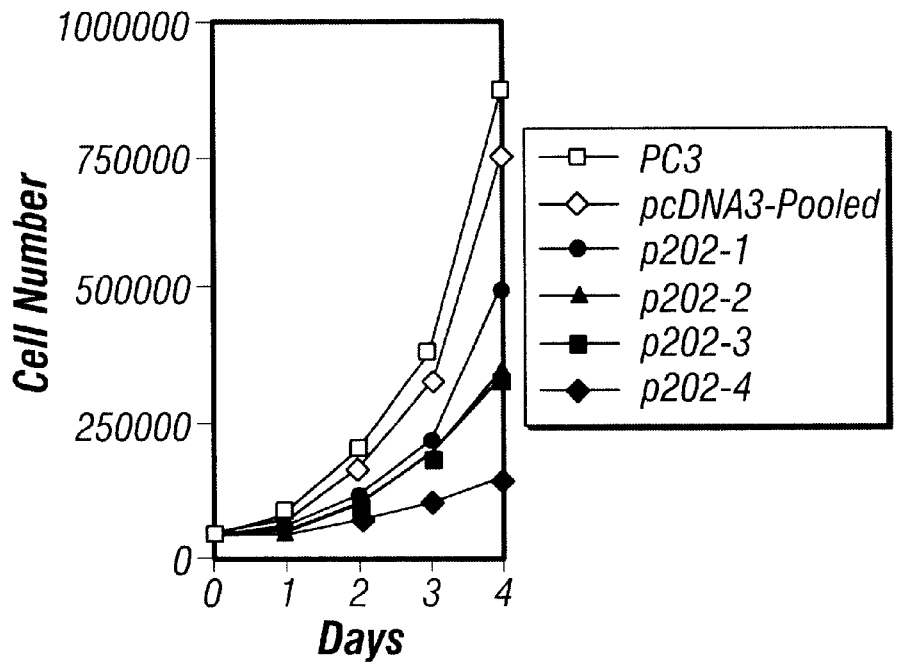
FIG. 9A and FIG. 9B. The reduced growth rate of the p202-expressing PC-3 cells. Four p202-expressing PC-3 stable cell lines, p202-1, -2, -3, and -4, as well as the controls, PC-3 and pcDNA3-pooled, were monitored for their growth characteristics.

To examine the growth inhibitory function of p202 in prostate cancer cells, the growth rates of the p202-expressing PC-3 cells with that of the control cells were compared. FIG. 9A shows that the high expressors, p202-2, -3, and -4 have a significantly slower growth rate than that of the controls, i.e. PC-3 and the pcDNA3-pooled, suggesting that the expression of p202 may be responsible for the decreased growth rate in PC-3 cells. It is interesting to note that p202-1, which has a modest level of p202 expression, grew at an intermediate rate between the high expressors and the control cell lines, suggesting a p202 dose-dependent growth inhibition.

Figure 9B:
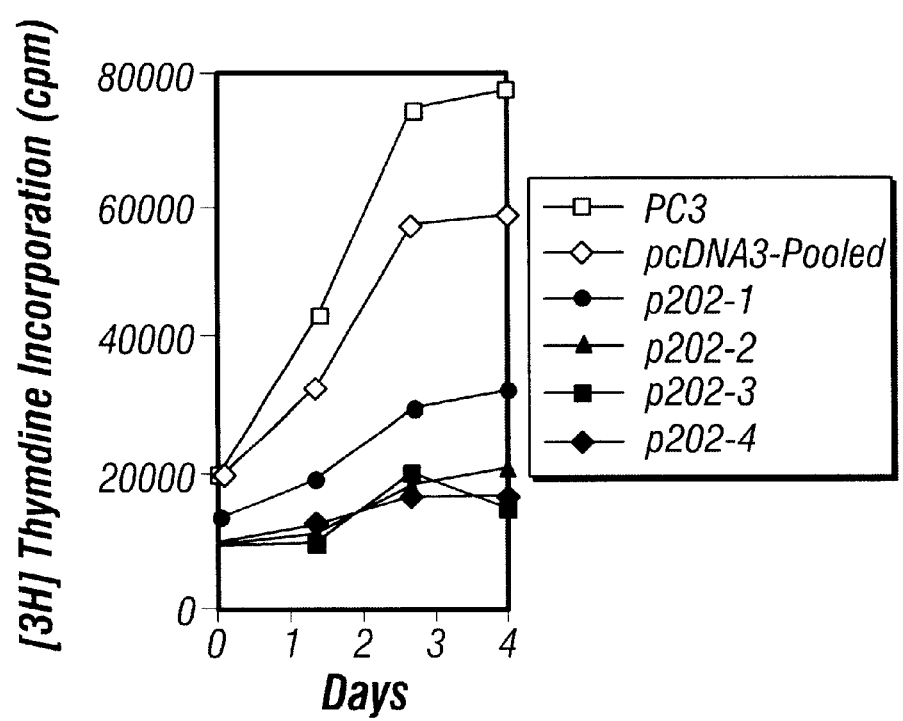

Another growth assay, MTT assay (Hansen et al., 1989), was also performed in these cell lines and the p202-expressing cells also showed a reduced growth characteristics than the control cell lines. Since the growth rate is the net result of two competing processes, i.e., cell replication and cell death, it is possible that the reduced growth rates may be caused by the p202-induced anti-cell replication and/or apoptosis in these cells. To test these possibilities, the percentage of the apoptotic cells in each asynchronized cell population was measured by Flow Cytometry Analysis. No significant apoptosis could be observed in all these cell lines under the normal growth condition, suggesting that apoptosis may not play a significant role in the p202-mediated growth inhibition in PC-3 cells. Since DNA synthesis rate has been used as an indicator for the rate of cell replication (Yuh et al., 1993), it was then determined if p202 may inhibit cell growth by reducing the DNA synthesis rate in PC-3 cell. [$^3$H]-thymidine incorporation assay was employed to measure the DNA synthesis rate in each cell line. FIG. 9B shows that the high expressors, p202-2, -3, and -4 exhibited much slower DNA synthesis rate than that of the control cell lines. Again, p202-1 showed an intermediate rate of DNA synthesis. Taken together, the data strongly suggest that the p202-mediated growth retardation in PC-3 cells may be primarily resulted from a reduced rate of cell replication.

TABLE 4 p202 expression inhibits colony formation of two human prostate cancer cell lines, PC-3 and DU145.

| cell line | % reduction of G418-resistant colonies * | no. of p202-expressing colonies/ no. of G418-resistant colonies screened # |
|---|---|---|
| PC-3 | 92.6 ± 2.5 | 4/20 |
| DU145 | 97.9 ± 1.5 | 0/20 |

This table summarized data obtained from two independent experiments. * G418-resistant colonies obtained from CMV-p202 transfection as a percentage of the number of colonies obtained from pcDNA3 transfection. #p202-expressing colonies identified by western blot using p202 antibody.

Figure 10:
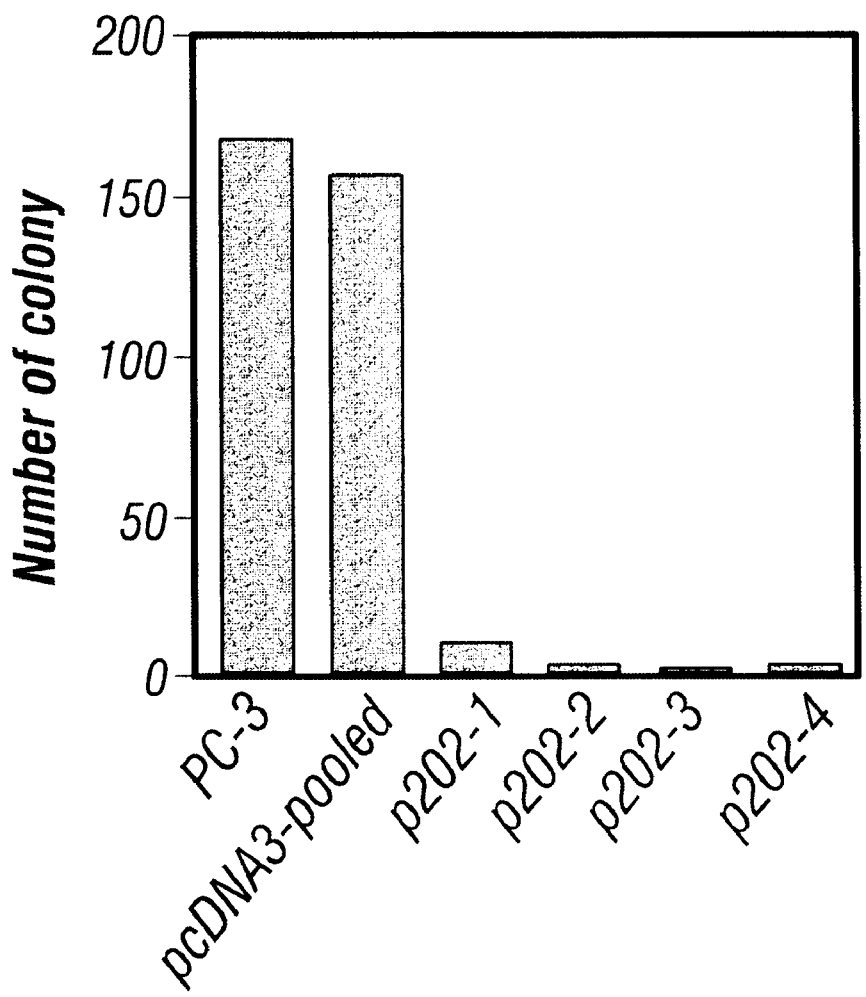
FIG. 10. The p202-expressing PC-3 cells exhibit poor growth in soft-agar. The p202-expressing PC-3 stable cell lines, p202-1, -2, -3, and -4, as well as the controls, PC-3 and pcDNA3-pooled, were monitored for their ability to grow in soft-agar. After three weeks of incubation, the colonies were visualized by staining with p-iodonitrotetrazolium violet. The bar diagram shows the number of soft agar colony formed by each cell line.

Example 7 p202 Expression Inhibits Anchorageindependent Growth of Human Prostate Cancer Cells Using an in vitro soft-agar colonization assay, it was observed that while the control cell lines, PC-3 and pcDNA3-pooled, could readily form colonies in soft agar, the p202-expressors, p202-1, -2, -3, and -4, showed a greatly reduced ability to form colonies in soft agar (FIG. 10). This result suggests that the p202 expression could diminish the ability of PC-3 to grow in an anchorage-independent manner. Interestingly, the modest expressor, p202-1, like the high expressors, has lost most of its ability to form colony in soft agar, suggesting that the expression of p202 is more potent in repressing transformation than in inhibiting cell growth.

The present invention describes that the IFN-α-inducible protein, p202, not only could inhibit the growth of human hormone-refractory prostate cancer cells by reducing the DNA synthesis rate in the cells but also could abolish the ability of these cells to grow in soft agar. Thus, the p202 expression may be responsible for the loss of transformation phenotype in these prostate cancer cells. The mechanisms by which p202 inhibits cell growth are not yet well defined. However, it is conceivable that the p202-mediated inhibition of DNA synthesis (Lembo, 1995) may be caused by the downregulation of the S-phase genes whose activation depends on the transactivation function of E2Fs. The expression of p202 abolishes E2F function because p202 interacts with the DNA binding domains of E2Fs, preventing E2Fs from activating the transcription of the S-phase genes. (Choubey et al., 1996; Choubey and Gutterman, 1997).

Figure 11A:
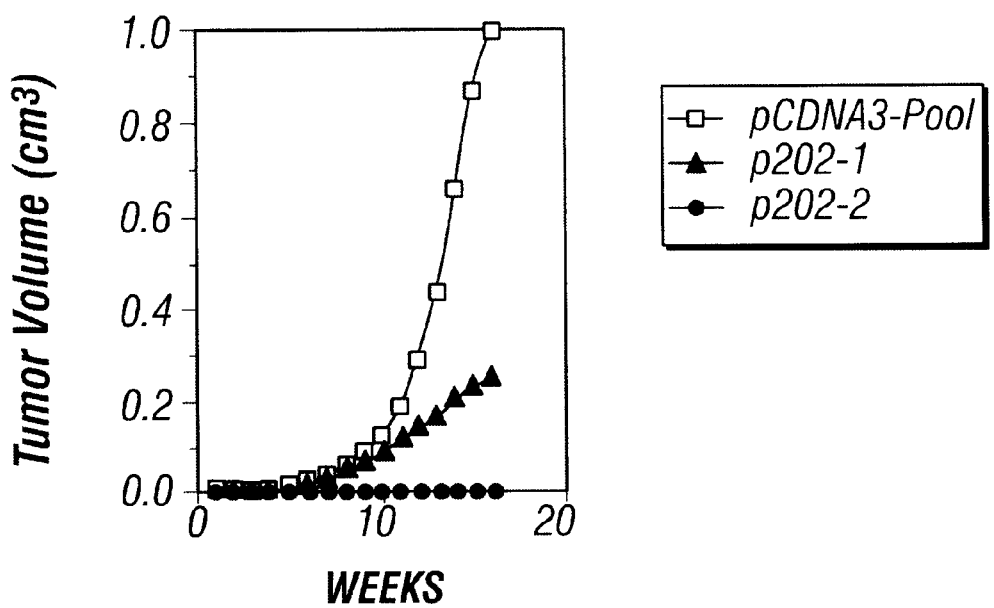
FIGS. 11A and 11B. Reduced tumorigenicity of p202-expressing PC-3 prostate cells.
Figure 11B:
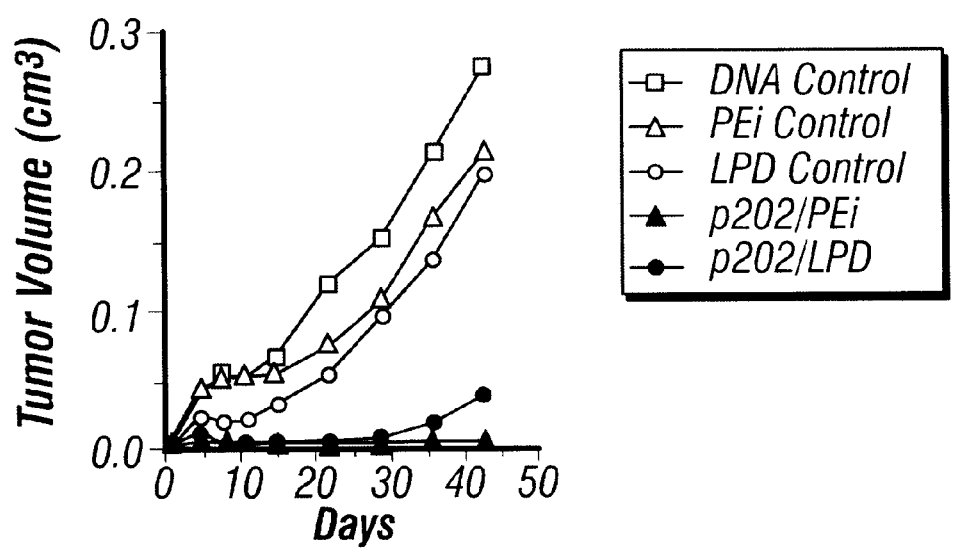

Example 8 p202 Expression Inhibits the Tumorigenicity of Human Prostate Cancer Cells In Vivo Nude mice were injected subcutaneously in the abdomen with p202-expressing PC-3 cells. FIG. 11A shows that tumor size was much reduced with p202-1 and p202-2 cells in comparison to pcDNA3 transfected pooled PC-3 controls. FIG. 11B shows the p202-mediated ex vivo reduction of PC-3 cell tumorigenicity. PC-3 cells transfected with CMV-p202 using either PEI or LPD liposome exhibited a much reduced tumor volume than control PC-3 cells.

Example 9 p202 Expression Inhibits Cell Growth in Ovarian Cancer Cells

The growth inhibitory effect of p202 on ovarian cancer cells was investigated by transfection of a p202 expression plasmid driven by CMV promoter (CMV-p202) in a control vector (pcDNA3) into SKOV3-IP1 cells. Since both plasmids contain a neomycin resistant gene, the number of G418-resistant colony by crystal violet staining was scored after three weeks of G418 selection. There was a dramatic reduction in the number of G418-resistant colony in cells p202 transfected cells as compared with that of the control transfection, pcDNA3.

Example 10 p202 Expression Inhibits Cell Growth in Human Pancreatic Cancer Cells

A p202 cDNA expression plasmid (CMV-p202) (Choubey et al., 1996) was transfected into Capan-1, Panc-1, BXPC-3, ASPC-1 and CFPAC-1. After G418 selection, the drug-resistant colonies were scored by crystal violet staining. A dramatic reduction (Table 5), in the number of G418-resistant colonies was observed in all cell lines transfected with CMV-p202 (p202) as compared to the pcDNA3 vector control.

It is possible that the reduction of colony numbers in p202-transfected pancreatic cancer cells may be caused by the p202-mediated growth retardation and/or apoptosis. To examine these possible mechanisms and to characterize the function of p202, the p202-expressing stable cell lines were isolated. For Panc-1 two clones that express p202 protein by western blot with a polyclonal antibody against p202 were identified: a moderate expressor, p202-1, and a very low expressor, p202-2. The control cell line colonies transfected with pcDNA3 vector have no detectable endogenous level of p202 protein. It has been previously shown that the p202 antibody also recognizes a 68 kd nonspecific protein which can be used as an internal control for normalizing the sample loading. (Coubey and Lengyel, 1993).

Figure 12A:
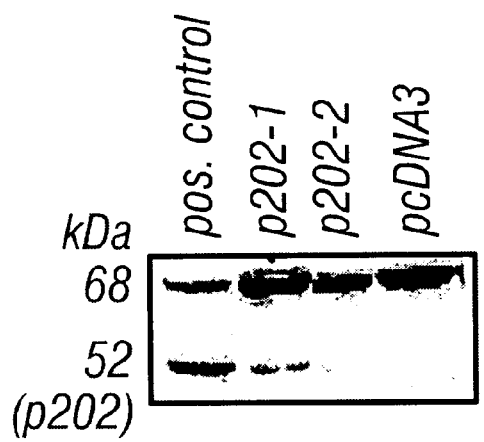
FIGS. 12A and B. The reduced growth rate of the p202-expressing Panc-1 cells. Two p202-expressing Pane-1 cell lines, p202-1 and -2, as well as the controls, Panc-1 and pcDNA3, were monitored for their growth characteristics.
Figure 12B:
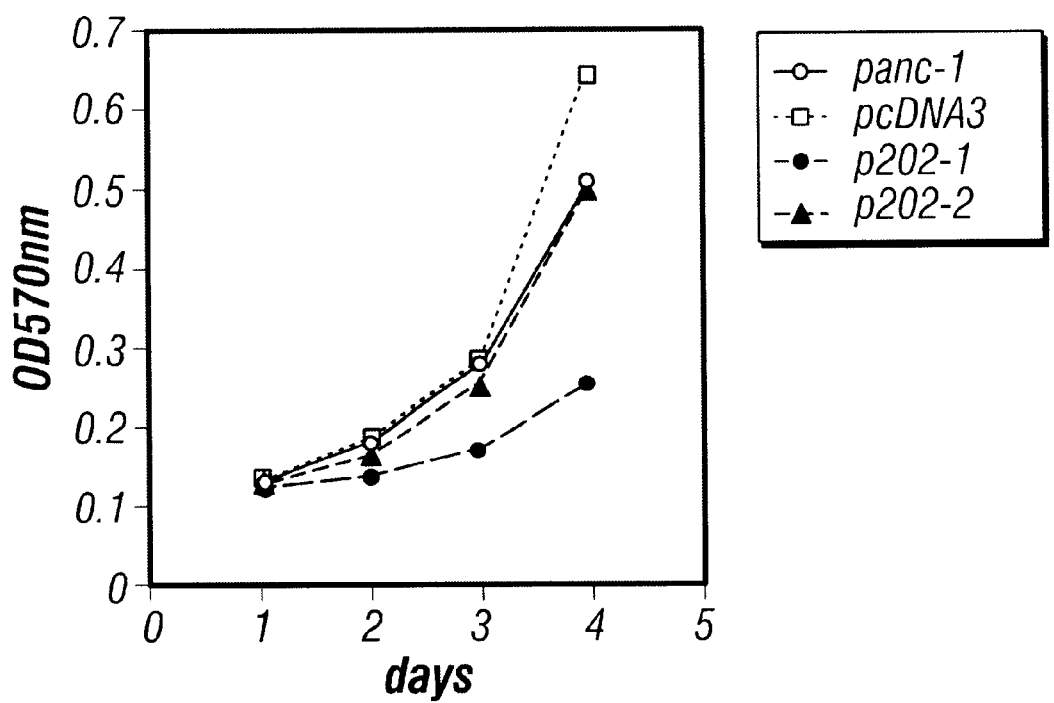
FIG. 12B: MTT assay. The growth rate of p202 expressing cells and the control cells were measured for four continuous days. Each measurement was conducted in quadruplicates. p202-1 grows much slower than the control cells.

To examine the growth inhibitory function of p202 in pancreatic cancer cells, the growth rates of the p202-expressing Panc-1 cells with that of the control cells were compared by MTT assay. FIG. 12A shows Western blot screening of the p202 stable transfectants. Two p202 expressing clones were identified, p202-1 and p202-2. The p202 expression of p202-2 is extremely low. FIG. 12B shows that the moderate expressor, p202-1, has a significantly slower growth rate than that of the controls, i.e. Panc-1 and pcDNA3, suggesting that the expression of p202 may be responsible for the decreased growth rate in Panc-1 cells. It is interesting to note that p202-2, which has a very low level of p202 expression, grew at an intermediate rate between the moderate expressor, p202-1, and the Panc-1 control, suggesting a p202 dose-dependent growth inhibition.

TABLE 5 p202 expression inhibits colony formation of five human pancreatic cancer cell lines, Capan-1, Panc-1, BXPC-3. ASPC-1 and CFPAC-1.

| cell line | pcDNA3* | p202# | % of control |
|---|---|---|---|
| Capan-1 | 130 | 3 | 2.3 |
| Panc-1 | 508 | 108 | 21.0 |
| BXPC-1 | 4 | 1 | 25.0 |
| ASPC-1 | 232 | 31 | 13.4 |
| CFPAC-1 | 6 | 0 | 0 |

*Colonies obtained from transfection of pancreatic cell lines with control vector DNA.
Colonies obtained from transfection of pancreatic cell lines with p202 DNA.

Figure 13A:
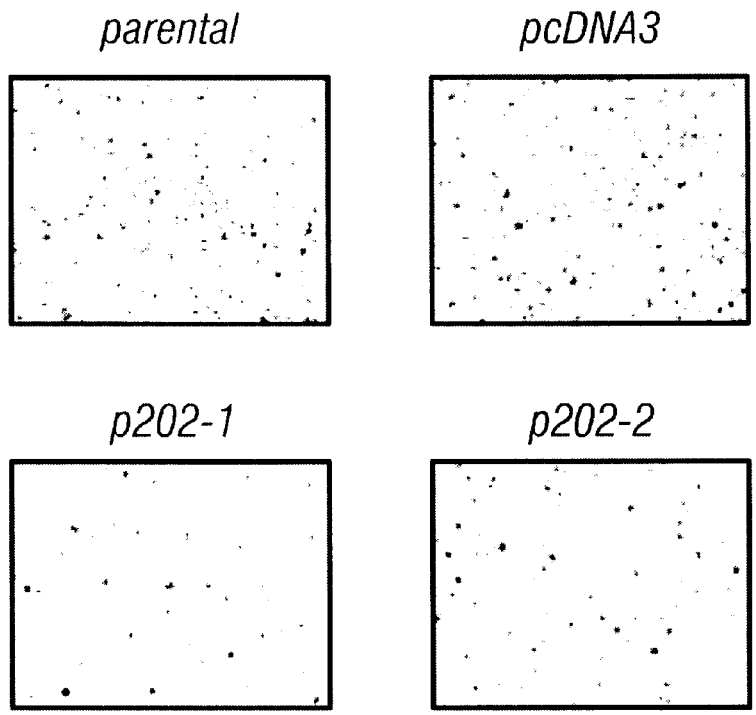
FIGS. 13A and B. p202 inhibits anchorageindependent cell growth of pancreatic cancer cells.
Figure 13B:
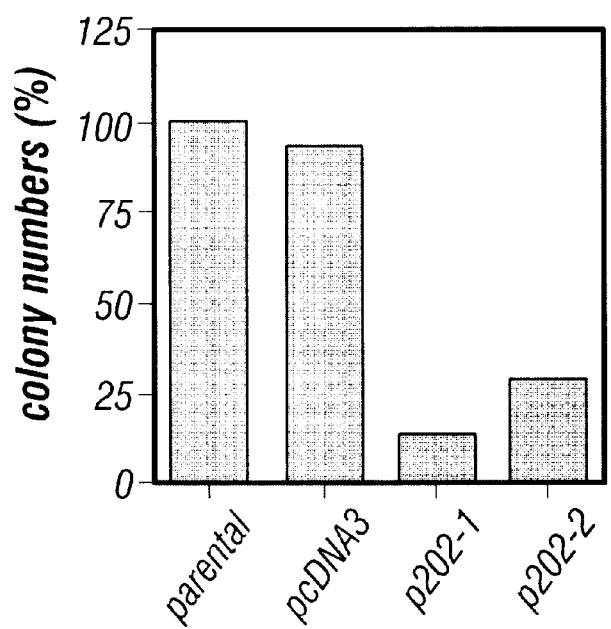
FIG. 13B: The bar diagram shows the number of colonies. The colony number in soft agar of the parental cells was presented as 100%. The experiments has been repeated three times with similar results.

Example 11 p202 Expression Inhibits Anchorageindependent Growth of Human Pancreatic Cancer Cells Using an in vitro soft-agar colonization assay, it was observed that while the controls, parental and pcDNA3, could readily form colonies in soft agar, the p202-expressors, p202-1 and -2, showed a greatly reduced ability to form colonies in soft agar (FIG. 13). This result indicates that p202 inhibits anchorage-independent cell growth, i.e., the in vitro transformation phenotype of pancreatic cancer cells. Interestingly, the very low expressor, p202-2, like the moderate expressor p-202-1, has lost most of its ability to form colony in soft agar, suggesting that the expression of p202 is more potent in repressing transformation than in inhibiting cell growth.

Figure 14A:
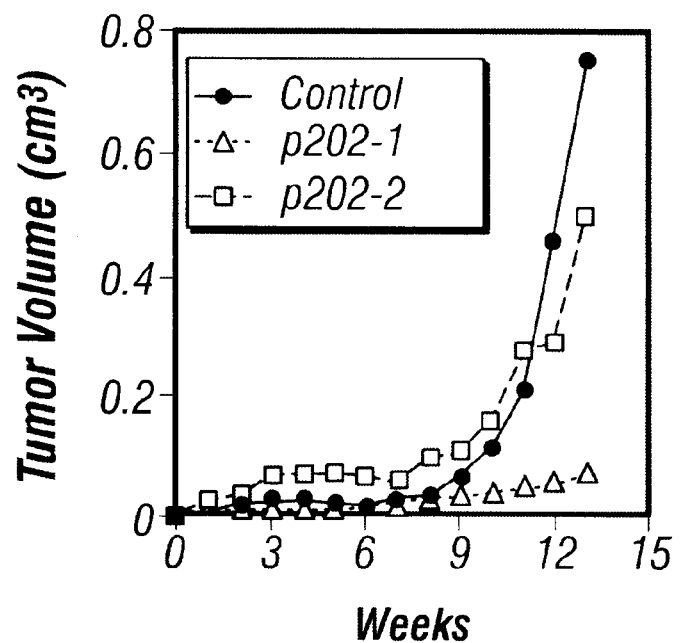
FIGS. 14A and B. Anti-tumor activity of p202 in pancreatic cancer cells.
Figure 14B:
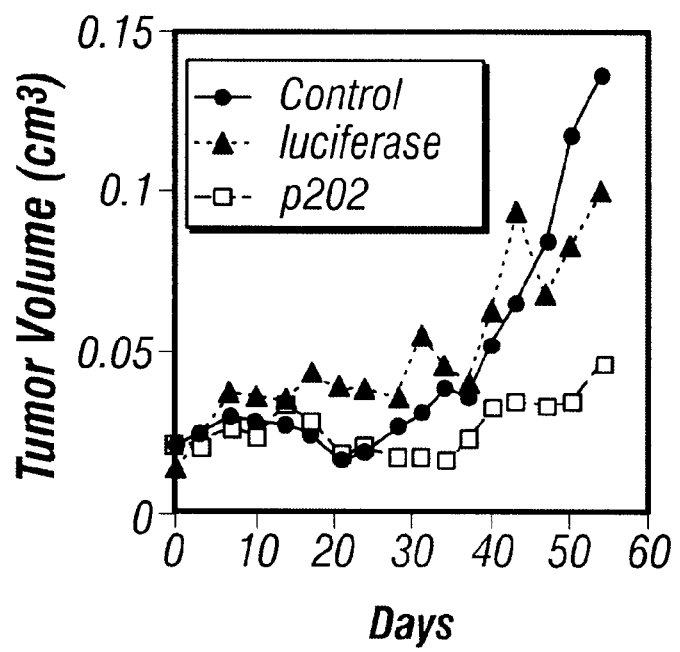
FIG. 14B: Suppression of the growth of xenograft pancreatic tumors in nude mice by p202 treatment. Nude mice were inoculated subcutaneously with panc-1 cells ($1 \times 10^6$ cells). When the tumors reached about 0.5 cm in diameter, intratumor injections of p202/SN2 complex were administered twice weekly. (SN2 is a liposome delivery vector in the inventors' lab.) Control groups were injected with SN2 alone or Luciferase/SN2 complex. The tumor growth was monitored twice a week.

Example 12 p202 Expression Inhibits the Tumorigenicity of Human Pancreatic Cancer Cells In Vivo Nude mice were injected subcutaneously in the abdomen with p202-expressing Panc-1 cells. FIG. 14A shows that tumor size was much reduced with moderate expressor p202-1 cells in comparison to controls. Very low expressor p202-2 cells show more moderate reduction in tumor size in comparison to controls. FIG. 14B shows suppression of the growth of xenograft pancreatic tumors in nude mice by p202 treatment. Nude mice were inoculated subcutaneously with panc-1 cells. After the tumors were about 0.5 cm in diameter, the mice were given intratumor injections with p202/SN2 complex twice a week. SN2 is a liposome delivery vector developed in the laboratory of the inventors. Control groups of mice were injected with SN2 alone or with luciferase/SN2 complex. Tumors treated with p202/SN2 showed significantly less tumor growth than controls.

Example 13

Human Treatment with p202

This example describes a protocol to facilitate the treatment of cancer using p202. A patient presenting a cancer may be treated using the following protocol. Patients may, but need not, have received previous chemo- radio- or gene therapeutic treatments. Optimally the patient will exhibit adequate bone marrow fuiction (defined as peripheral absolute granulocyte count of >2,000/mm3 and platelet count of 100, 000/mm3, adequate liver function (bilirubin 1.5 mg/dl) and adequate renal function (creatinine 1.5 mg/dl).
Cancer Treatment Protocol A composition of the present invention is typically administered orally or parenterally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, or infusion techniques. The p202 may be delivered to the patient alone or indeed in combination with other therapies. Where a combination therapy is contemplated, the p202 may be administered before, after or concurrently with the other anti-cancer agents.

A typical treatment course may comprise about six doses delivered over a 7 to 21 day period. Upon election by the clinician the regimen may be continued six doses every three weeks or on a less frequent (monthly, bimonthly, quarterly etc.) basis. Of course, these are only exemplary times for treatment, and the skilled practitioner will readily recognize that many other time-courses are possible.

In one embodiment, administration simply entails injection of the therapeutic composition into the tumor. In another embodiment, a catheter is inserted into the site of the tumor and the cavity may be continuously perfused for a desired period of time.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

Of course, the above-described treatment regimes may be altered in accordance with the knowledge gained from clinical trials such as those described in Example 14. Those of skill in the art will be able to take the information disclosed in this specification and optimize treatment regimes based on the clinical trials described in the specification.

Example 14

Clinical Trials of the Use of p202 in Treating Cancer

This example is concerned with the development of human treatment protocols using the p202. Such drug treatment will be of use in the clinical treatment of various cancers in which transformed or cancerous cells play a role. Such treatment will be particularly useful tools in anti-tumor therapy, for example, in treating patients with ovarian, breast and prostate cancers that are resistant to conventional chemotherapeutic regimens.

The various elements of conducting a clinical trial, including patient treatment and monitoring, will be known to those of skill in the art in light of the present disclosure. The following information is being presented as a general guideline for use in establishing p202 in clinical trials.

Patients with advanced, metastatic breast and/or epithelial ovarian carcinoma chosen for clinical study will typically have failed to respond to at least one course of conventional therapy. Measurable disease is not required, however the patient must have easily accessible pleural effusion and/or ascites. In an exemplary clinical protocol, patients may undergo placement of a Tenckhoff catheter, or other suitable device, in the pleural or peritoneal cavity and undergo serial sampling of pleural/peritoneal effusion. Typically, one will wish to determine the absence of known loculation of the pleural or peritoneal cavity, creatinine levels that are below 2 mg/dl, and bilirubin levels that are below 2 mg/dl. The patient should exhibit a normal coagulation profile.

In regard to the p202 and/or other anti-cancer drug administration, a Tenckhoff catheter, or alternative device may be placed in the pleural cavity or in the peritoneal cavity, unless such a device is already in place from prior surgery. A sample of pleural or peritoneal fluid can be obtained, so that baseline cellularity, cytology, LDH, and appropriate markers in the fluid (CEA, CA15-3, CA 125, p185) and in the cells (PEA3, p185) may be assessed and recorded.

In the same procedure, p202 may be administered alone or in combination with the another chemotherapeutic agent. The administration may be in the pleural/peritoneal cavity, directly into the tumor, or in a systemic manner. The starting dose may be 0.5 mg/kg body weight. Three patients may be treated at each dose level in the absence of grade >3 toxicity. Dose escalation may be done by 100% increments (0.5 mg, 1 mg, 2 mg, 4 mg) until drug related grade 2 toxicity is detected. Thereafter dose escalation may proceed by 25% increments. The administered dose may be fractionated equally into two infusions, separated by six h if the combined endotoxin levels determined for the lot of p202 and the lot of anti-cancer drug exceed 5 EU/kg for any given patient.

The p202 and/or anti-cancer agent combination may be administered over a short infusion time or at a steady rate of infusion over a 7 to 21 day period. The p202 infusion may be administered alone or in combination with the anti-cancer drug. The infusion given at any dose level will be dependent upon the toxicity achieved after each. Hence, if Grade II toxicity was reached after any single infusion, or at a particular period of time for a steady rate infusion, further doses should be withheld or the steady rate infusion stopped unless toxicity improved. Increasing doses of p202 in combination with an anti-cancer drug will be administered to groups of patients until approximately 60% of patients show unacceptable Grade III or IV toxicity in any category. Doses that are ⅔ of this value could be defined as the safe dose.

Physical examination, tumor measurements, and laboratory tests should, of course, be performed before treatment and at intervals of about 3–4 weeks later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum should be monitored e.g. CEA, CA 15-3, p185 for breast cancer, and CA 125, p185 for ovarian cancer To monitor disease course and evaluate the anti-tumor responses, it is contemplated that the patients should be examined for appropriate tumor markers every 4 weeks, if initially abnormal. With twice weekly CBC, differential and platelet count for the 4 weeks; then, if no myelosuppression has been observed, weekly. If any patient has prolonged myelosuppression, a bone marrow examination is advised to rule out the possibility of tumor invasion of the marrow as the cause of pancytopenia. Coagulation profile shall be obtained every 4 weeks. An SMA-12–100 shall be performed weekly. Pleural/peritoneal eff-usion may be sampled 72 h after the first dose, weekly thereafter for the first two courses, then every 4 weeks until progression or off study. Cellularity, cytology, LDH, and appropriate markers in the fluid (CEA, CA15-3, CA 125, p185) and in the cells (p185) may be assessed. For an example of an evaluation profile, see Table 6. When measurable disease is present, tumor measurements are to be recorded every 4 weeks. Appropriate radiological studies should be repeated every 8 weeks to evaluate tumor response. Spirometry and DLCO may be repeated 4 and 8 weeks after initiation of therapy and at the time study participation ends. An urinalysis may be performed every 4 weeks.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

TABLE 6

Evaluations Before and During Therapy

| EVALUATIONS | PRE-STUDY | TWICE WEEKLY | WEEKLY | EVERY 4 WEEKS | EVERY 8 WEEKS |
|---|---|---|---|---|---|
| History | X | | | X | |
| Physical | X | | | X | |
| Tumor Measurements | X | | | X | |
| CBC | X | X[1] | X | | |
| Differential | X | X[1] | X | | |
| Platelet Count | X | X[1] | X | | |
| SMA12-100 (SGPT, Alkaline Phosphatase, Bilirubin, Alb/Total Protein) | X | | | X | |
| Coagulation Profile | X | | | X | |
| Serum Tumor markers (CEA, CA15-3, CA-125, Her-2/neu) | X | | | X[3] | |
| Urinalysis | X | | | X | |
| X-rays: | | | | | |
| Chest | X | | X[4] | | |
| Others | X | | | | X |
| Pleural/Peritoneal Fluids: (cellularity, cytology, LDH, tumor markers, E1A, HER-2/neu) | X | | X[5] | X | |
| Spirometry and DLCO | X | | | X[6] | X[6] |

[1] For the first 4 weeks, then weekly, if no myelosuppression is observed.
[2] As indicated by the patient's condition.
[3] Repeated every 4 weeks if initially abnormal.
[4] For patients with pleural effusion, chest X-rays may be performed at 72 h after first dose, then prior to each treatment administration.
[5] Fluids may be assessed 72 h after the first dose, weekly for the first two courses and then every 4 weeks thereafter.
[6] Four and eight weeks after initiation of therapy.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adelman et al., DNA, 2:183, 1983.
Ahre et al., Eur. J. Haematol., 41:123–130, 1988.
Baichwal and Sugden, In: Gene Transfer, Kucherlapati R, (ed.)New York: Plenum Press, pp. 117–148, 1986.
Barany and Menyfield, In: The Peptides, Gross and Meienhoefer, eds, Academmic Press, New York, pp 1–284, 1979.
Beg and Baltimore, Science, 274:782–784, 1996.
Belldegrun, Cancer, 77:1862–1872, 1996.
Benvenisty and Reshel, Proc. Nat. Acad. Sci. USA, 83:9551–9555, 1986.
Boussif et al., Proc. Nat'l. Acad. Sci. USA., 92:7297–7301, 1995.
Brinster et al., Proc. Nat'l Acad. Sci. USA, 82:4438–4442, 1985.
Chang et al, Hepatology, 14:124A, 1991.
Chen and Okayama, Mol. Cell Biol., 7:2745–2752, 1987.
Choubey and Gutterman, Biochem. Biophys. Res. Commun., 221:396–401, 1996.
Choubey and Gutterman, Oncogene., 15: 291–301, 1997.
Choubey and Lengyel, J. Biol. Chem., 270:6134–6140, 1995.
Choubey, and Lengyel, J. Interferon. Res., 13:43–52, 1993.
Choubey et al., EMBO J., 15:5668–5678, 1996.
Choubey et al., J. Biol. Chem., 264:17182–17189, 1989.
Coffin, In: Virology, Fields et al. (eds.), New York: Raven Press, pp. 1437–1500, 1990.
Cohen, "Apoptosis," Immunol. Today, 14(3): 126–130, 1993.
Coradini et al., Anticancer Res., 14:1779–1784, 1994.
Coradini et al., Anticancer Res., 18:177–182, 1998.
Couch et al., Am. Rev. Resp. Dis., 88:394–403, 1963.
Coupar et al., Gene, 68:1–10, 1988.
Crea et al., Proc. Natl. Acad. Sci. U.S.A., 75:5765, 1978.
Culver et al., Science, 256:1550–1552, 1992.
Datta et al., J. Biol. Chem., 271:27544–27555, 1996
Datta et al., Mol. Cell. Biol., 18:1074–1083, 1998.
Dubensky et al., Proc. Nat'l Acad. Sci. USA, 81:7529–7533, 1984.
Eichenlaub, J. Bacteriol, 138:559–566, 1979.
Ellisen and Haber, Science and Medicine, July/August, 26–35, 1998.

Evan and Littlewood, *Science*, 281:1317–21, 1998.
Ezekowitz et al., *N. Engl. J. Med.*, 326:1456–1463, 1992.
Fechheimer et al., *Proc. Nat'l Acad. Sci. USA*, 84:8463–8467, 1987.
Ferkol et al., *FASEB J.*, 7:1081–1091, 1993.
Foulds, *J. Chronic Dis.*, 8:2–37, 1958.
Fraley et al., *Proc. Nat'l Acad. Sci. USA*, 76:3348–3352, 1979.
Friedmann, *Science*, 244:1275–1281, 1989.
Gao et al., *Biochemical and Biophysical Research Communications*, 179(1):280–285, 1991.
Ghosh and Bachhawat, In: *Liver Diseases, Targeted Diagnosis and Therapy Using Specific Receptors and Ligands*, Wu et al., (eds.), Marcel Dekker, New York, pp. 87–104, 1991.
Gomez-Foix et al., *J. Biol. Chem.*, 267:25129–25134, 1992.
Gottardis et al., *J. Steroid Biochem*, 30:311–314, 1988.
Graham and Prevec, *Biotechnology*, 20:363–390, 1992.
Graham and van der Eb, *Virology*, 52:456–467, 1973.
Gribskov et al. (1986), *Nucl. Acids Res.*, 14:6745.
Grunhaus and Horwitz, *Seminar in Virology*, 3:237–252, 1992.
Grzegorzewski et al., *Cancer Commun.*, 1:373–379, 1989.
Gutterman and Choubet, *Cell Growth Differ.*, 10:93–100 (1999).
Gutterman, *Proc. Natl. Acad. Sci. U.S.A.*, 91:1198–1205, 1994.
Hansen et al., *J. Immunol. Methods*, 119(2):203–10, 1989.
Harland and Weintraub, *J. Cell Biol*, 101:1094–1099, 1985.
Harlow and Lane, Antibodies: *A Laboratory manual*, Cold Spring Harbor Laboratory, 1988.
Hermonat and Muzycska, *Proc. Nat'l Acad. Sci. USA*, 81:6466–6470, 1984.
Herz and Gerard, *Proc. Nat'l Acad. Sci. USA*, 90:2812–2816, 1993.
Horwich et al., *J. Virol.*, 64:642–650, 1990.
Kalderon et al., *Virology*, 139:109–137, 1984.
Kaneda et al., *Science*, 243:375–378, 1989.
Kato et al., *J. Biol Chem.*, 266:3361–3364, 1991.
Kirkwood et al., *Cancer Res.*, 45: 863–871, 1985.
Klein et al., *Nature*, 327:70–73, 1987.
Koul et al., *Biochem. Biophys. Res. Commun.*, 247:379–382, 1998.
Kull and Cuatrecasas, *Cancer. Res.*, 41:4885–4890, 1981.
Le Gal La Salle et al., *Science*, 259:988–990, 1993.
Lee et al., *Science*, 235:1394–1399, 1987.
Lembo et al., *J. Biol. Regul. Homeost. Agents*, 9:42–46, 1995.
Levrero et al., *Gene*, 101: 195–202, 1991.
In: *Manipulating the Mouse Embryo: A Laboratory Manual*, $2^{nd}$ Ed., Hogan et al., (eds.), Cold Spring Harbor Laboratory Press, 1994.
Mann et al., *Cell*, 33:153–159, 1983.
Meryfield, *Science*, 232:341–347, 1986.
Messing et al., *Third Cleveland Symposium on Macromolecules and Recombinant DNA*, Editor A. Walton, Elsevier, Amsterdam, 1981.
Min et al., *Mol. Cell. Biol.*, 16:359–368, 1996.
Nabel et al., *Science*, 249:1285–1288, 1990.
Needleman et al., *J. Mol. Biol.*, 48:443, 1970.
Nicolas and Rubenstein, In: *Vectors: A survey of molecular cloning vectors and their uses*, Rodriguez and Denhardt (eds.), Stoneham: Butterworth, pp. 493–513, 1988.
Nicolau and Sene, *Biochem. Biophys. Acta*, 721:185–190, 1982.
Nicolau et al., *Methods in Enzymology*, 149:157–176, 1987.
Oettgen et al., *Immunobiology*, 172: 269–274, 1986.
Paskind et al., *Virology*, 67:242–248, 1975.
Perales et al., *Proc. Natl. Acad. Sci. USA*, 91:4086–4090, 1994.
Potter et al., *Proc. Nat'l Acad. Sci. USA*, 81:7161–7165, 1984.
Ragot et al., *Nature*, 361:647–650, 1993.
Rich et al., *Hum. Gene Ther.*, 4:461–476, 1993.
Ridgeway, In: Vectors: *A survey of molecular cloning vectors and their uses*. Rodriguez RL, Denhardt DT, (eds.), Stoneham: Butterworth, pp. 467–492, 1988.
Rippe et al., *Mol. Cell Biol.*, 10:689–695, 1990.
Rosenfeld et al., *Cell*, 68:143–155, 1992.
Rosenfeld et al., *Science*, 252:431434, 1991.
Roux et al., *Proc. Natl. Acad. Sci. USA*, 86:9079–9083, 1989.
Sambrook et al., *Molecular Cloning: A Laboratory Manual*, 2d Ed., Cold Spring Harbor Laboratory Press, Cold Spring Harbor, N.Y., 1989.
Sentman et al., *Cell*, 67(5):879–888, 1991.
Smith et al., *Cell*, 76(6):959–962, 1994.
Smith et al., *Adv. Appl. Math.*, 2:482, 1981.
Sokoloff et al., *Cancer*, 77:1862–1872, 1996.
Stratford-Perricaudet and Perricaudet, In: Human Gene Transfer, O. Cohen-Haguenauer and M. Boiron, (eds.), Editions John Libbey Eurotext, France, pp. 51–61, 1991.
Stratford-Perricaudet et al., *Hum. Gene Ther.*, 1:241–256, 1990.
Stewart and Young, Solid Phase peptide Synthesis, 2d. ed., Pierce Chemical Co., 1984.
Suda et al., *Cell*, 75(6):1169–1178, 1993.
Sugarman et al., *Science*, 230:943–945, 1985.
Tam et al., *J. Am. Chem Soc.*, 105:6442, 1983.
Temin, In: Gene Transfer, Kucherlapati (ed.), New York: Plenum Press, pp. 149–188, 1986.
Top et al., *J. Infect. Dis.*, 124:155–160, 1971.
Tur-Kaspa et al., *Mol. Cell Biol*, 6:716–718, 1986.
Van Antwerp et al., *Science*, 274:787–789, 1996.
Varmus et al., *Cell*, 25:23–36, 1981.
Vogelstein et al., *Genes Chromosomes Cancer*, 2(2):159–162, 1990.
Wagner et al., *Science*, 260:1510–1513, 1990.
Wang et al., *Science*, 274:784–787, 1996.
Weinberg, *Biochemistry*, 28:8263–8269, 1989.
Williams and Smith, *Cell*, 74(5):777–779, 1993.
Wiseman and Spencer, *Drugs Aging*, 12:305–34, 1998.
Wu and Wu, *Biochemistry*, 27:887–892, 1988.
Wu and Wu, *J. Biol. Chem.*, 262:4429–4432, 1987.
Wu et al., *Genomics*, 4:560, 1989.
Yan et al., *Oncogene.*, 18:807–811, 1999.
Yang et al., *Proc. Natl. Acad. Sci. USA*, 87:9568–9572, 1990.
Yu et al., *Cancer Res.*, 53(4):891–8, 1993.
Zelenin et al., *FEBS Lett.*, 280:9496, 1991.

What is claimed is:

1. A method for repressing transformation in a cell, the method comprising contacting said cell with a p202 polypeptide in an amount effective to inhibit a transformed phenotype.

2. The method of claim 1, wherein said p202 polypeptide is introduced into said cell by the direct introduction of said p202 polypeptide.

3. The method of claim 1, wherein said p202 polypeptide is introduced into the cell through the introduction of a p202-encoding polynucleotide.

4. The method of claim 1, wherein the tumorigenic potential of the cell is suppressed.

5. The method of claim 1, wherein the metastatic potential of the cell is suppressed.

6. The method of claim 1, wherein the cell is a human cell.

7. The method of claim 1, wherein the cell is a tumor cell.

8. The method of claim 1, further comprising treating the cell with a second agent, wherein the second agent is a therapeutic polypeptide, polynucleotide encoding a therapeutic polypeptide, chemotherapeutic agent, or radiotherapeutic agent.

9. The method of claim 1, wherein said cell is in an animal.

10. The method of claim 1, wherein the p202 polypeptide is administered by injection.

11. The method of claim 3, wherein said polynucleotide is a deoxyribonucleic acid molecule that encodes a p202 polypeptide.

12. The method of claim 3, wherein said p202-encoding polynucleotide further comprises control sequences operatively linked to said p202 encoding polynucleotide.

13. The method of claim 2, wherein said p202-encoding polynucleotide is located on a vector.

14. The method of claim 12, wherein said polynucleotide is operably linked to a promoter.

15. The method of claim 14, wherein said promoter is selected from the group consisting of CMV IE, SV40 IE, RSV, and β-actin.

16. The method of claim 13, wherein said vector comprises a plasmid vector.

17. The method of claim 13, wherein said vector comprises a viral vector.

18. The method of claim 17, wherein said viral vector is selected from the group consisting of retrovirus, adenovirus, herpesvirus, vaccinia virus, and adeno-associated virus.

19. The method of claim 7, wherein the tumor cell is selected from the group consisting of a breast tumor cell, an ovarian tumor cell, a prostate tumor cell, and a pancreatic tumor cell.

20. The method of claim 8, wherein the second agent is a therapeutic polypeptide and the therapeutic polypeptide is TNFα.

21. The method of claim 8, wherein the second agent is a polynucleotide encoding a therapeutic polypeptide and the polynucleotide encodes a TNFα polypeptide.

22. The method of claim 8, wherein said chemotherapeutic agent is taxol.

23. The method of claim 9 wherein said animal is a human.

24. A method for inhibiting tumor cell proliferation comprising contacting a tumor cell with a p202 polypeptide in an amount effective to inhibit tumor cell proliferation.

25. The method of claim 24, wherein said p202 polypeptide is introduced into said cell by the direct introduction of said p202 polypeptide.

26. The method of claim 24, wherein said p202 polypeptide is introduced into the cell through the introduction of a p202-encoding polynucleotide.

27. The method of claim 24, further comprising treating the cell with a second agent, wherein the second agent is a therapeutic polypeptide, polynucleotide encoding a therapeutic polypeptide, chemotherapeutic agent, or radiotherapeutic agent.

28. The method of claim 24, wherein said tumor cell is a human tumor cell.

29. The method of claim 24, wherein said tumor cell is selected from the group consisting of a breast tumor cell, an ovarian tumor cell, a prostate tumor cell, and a pancreatic tumor cell.

30. The method of claim 24, wherein said p202 polypeptide is administered by injection.

31. The method of claim 26, wherein said polynucleotide is a deoxyribonucleic acid molecule that encodes a p202 polypeptide.

32. The method of claim 26, wherein said p202-encoding polynucleotide further comprises control sequences operatively linked to said p202 encoding polynucleotide.

33. The method of claim 26, wherein said p202-encoding polynucleotide is located on a vector.

34. The method of claim 32, wherein said polynucleotide is operably linked to a promoter.

35. The method of claim 34, wherein said promoter is selected from the group consisting of CMV IE, SV40 IE, RSV and β-actin.

36. The method of claim 33, wherein said vector comprises a plasmid vector.

37. The method of claim 36, wherein said vector comprises a viral vector.

38. The method of claim 37, wherein said viral vector is selected from the group consisting of retrovirus, adenovirus, herpesvirus, vaccinia virus, and adeno-associated virus.

39. The method of claim 27, wherein said polypeptide is TNFα.

40. The method of claim 27, wherein said polynucleotide encodes a TNFα polypeptide.

41. The method of claim 27, wherein said chemotherapeutic agent is taxol.

42. The method of claim 27, wherein said second therapeutic agent induces apoptosis.

43. The method of claim 27, wherein said method induces apoptosis.

44. The method of claim 29, wherein said tumor cell is in a tumor.

45. The method of claim 44, wherein said tumor is in an animal.

46. The method of claim 45, wherein said animal is a human.

47. A method for altering the phenotype of a tumor cell comprising contacting said tumor cell with a p202 polypeptide in an amount effective to alter the phenotype of said tumor cell.

48. The method of claim 47, wherein said phenotype is selected from the group consisting of proliferation, soft agar growth, migration, contact inhibition, and cell cycling.

49. The method of claim 47, wherein said p202 polypeptide is introduced into said cell by the direct introduction of said p202 polypeptide.

50. The method of claim 47, wherein said p202 polypeptide is introduced into the cell through the introduction of a p202-encoding polynucleotide.

51. The method of claim 47, wherein said tumor cell is a human tumor cell.

52. The method of claim 47, wherein the tumor cell is selected from the group consisting of a breast tumor cell, an ovarian tumor cell, a prostate tumor cell, and a pancreatic tumor cell.

53. The method of claim 47, wherein the tumor cell is in a tumor.

54. The method of claim 47, wherein the p202 polypeptide is administered by injection.

55. The method of claim 50, wherein said polynucleotide is a deoxyribonucleic acid molecule that encodes a p202 polypeptide.

56. The method of claim 50, wherein said p202-encoding polynucleotide further comprises control sequences operatively linked to said p202 encoding polynucleotide.

57. The method of claim 50, wherein said p202-encoding polynucleotide is located on a vector.

58. The method of claim 56, wherein said polynucleotide is operably linked to a promoter.

59. The method of claim 58, wherein said promoter is selected from the group consisting of CMV IE, SV40 IE, RSV, and β-actin.

60. The method of claim 57, wherein said vector comprises a plasmid vector.

61. The method of claim 57, wherein said vector comprises a viral vector.

62. The method of claim 61, wherein said viral vector is selected from the group consisting of retrovirus, adenovirus, herpesvirus, vaccinia virus, and adeno-associated virus.

63. The method of claim 53, wherein the tumor is in an animal.

64. The method of claim 63, wherein the animal is a human.

65. A therapeutic kit comprising in suitable container, a pharmaceutical formulation of a p202 gene product or a polynucleotide encoding a p202 gene product.

66. The therapeutic kit of claim 65, further comprising a pharmaceutical formulation of a therapeutic polypeptide, polynucleotide encoding a therapeutic polypeptide, or chemotherapeutic agent.

* * * * *

UNITED STATES PATENT AND TRADEMARK OFFICE
CERTIFICATE OF CORRECTION

PATENT NO. : 6,331,284 B1  Page 1 of 1
DATED : December 18, 2001
INVENTOR(S) : Hung et al.

It is certified that error appears in the above-identified patent and that said Letters Patent is hereby corrected as shown below:

Column 55,
Line 42, please delete "2" and insert -- 3 -- therefor.

Column 56,
Line 39, please delete "polynucleotide" and insert -- polypeptide -- therefor.

Signed and Sealed this

Eighteenth Day of June, 2002

Attest:

JAMES E. ROGAN
Attesting Officer  Director of the United States Patent and Trademark Office